(12) United States Patent
Farris et al.

(10) Patent No.: US 6,485,491 B1
(45) Date of Patent: Nov. 26, 2002

(54) POSTERIOR FIXATION SYSTEM

(75) Inventors: Robert A. Farris, Cordova, TN (US); Kevin T. Foley, Germantown, TN (US); Stephen M. Papadopoulos, Ann Arbor, MI (US); Jeffrey Wade Poyner, Atoka, TN (US); Ricardo Sasso, Indianapolis, IN (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 09/663,638

(22) Filed: Sep. 15, 2000

(51) Int. Cl.$^7$ ............................................. A61B 17/70
(52) U.S. Cl. ......................................... 606/61; 606/72
(58) Field of Search ..................... 606/60, 61, 69, 606/72, 73; 623/17.11, 17.16

(56) References Cited

U.S. PATENT DOCUMENTS

| | | | |
|---|---|---|---|
| 4,763,644 A | 8/1988 | Webb | |
| 4,805,602 A | * 2/1989 | Puno et al. | 606/73 |
| 4,841,959 A | 6/1989 | Ransford | |
| 4,867,144 A | 9/1989 | Karas et al. | |
| 4,887,595 A | 12/1989 | Heinig et al. | |
| 4,946,458 A | 8/1990 | Harms et al. | |
| 5,005,562 A | 4/1991 | Cotrel | |
| 5,084,049 A | 1/1992 | Asher et al. | |
| 5,085,660 A | 2/1992 | Lin | |
| 5,092,893 A | 3/1992 | Smith | |
| 5,133,716 A | 7/1992 | Plaza | |
| 5,176,678 A | 1/1993 | Tsou | |
| 5,207,678 A | 5/1993 | Harms et al. | |
| 5,261,909 A | 11/1993 | Sutterlin et al. | |
| 5,312,405 A | 5/1994 | Korotko et al. | |
| 5,330,477 A | 7/1994 | Crook | |
| 5,360,431 A | * 11/1994 | Puno et al. | 606/72 |
| 5,364,399 A | 11/1994 | Lowery et al. | |
| 5,437,671 A | 8/1995 | Lozier et al. | |
| 5,443,467 A | 8/1995 | Biedermann et al. | |
| 5,466,237 A | 11/1995 | Byrd, III et al. | |
| 5,470,333 A | 11/1995 | Ray | |
| 5,474,555 A | * 12/1995 | Puno et al. | 606/73 |

(List continued on next page.)

FOREIGN PATENT DOCUMENTS

| | | |
|---|---|---|
| DE | 195 09 332 | 8/1996 |
| DE | 197 20 782 | 11/1998 |
| GB | 2 173 104 A | 10/1996 |

Primary Examiner—Pedro Philogene
(74) Attorney, Agent, or Firm—Woodard, Emhardt, Naughton, Moriarty & McNett

(57) ABSTRACT

A posterior fixation system includes a saddle member, an anchoring member, an occipital plate, an occipital rod, and a cross-link connector. The anchoring member anchors the saddle member to bone. The saddle member includes a pair of upright portions that define a channel. The channel is adapted to receive an orthopedic rod, and the saddle member can include a hole to receive the anchoring member. The saddle member and the anchoring member can be coupled so as to allow multi-axial movement of the members. The anchoring member in one embodiment is a screw coupled to the hole of the saddle, and in another embodiment, the anchoring member is a hook. The offset member may be coupled to the saddle member to allow for offset connection of rods. Connection of individual rods can be accomplished by connecting the rods with the cross-link connector. The cross-link connector has an integrally formed cylindrical member that couples a pair of coupling portions together. The cylindrical member can be bent along multiple axes. The occipital plate secures the rods to the occipital bone of the skull. The occipital plate has a cross-shaped plate with a plurality of apertures defined in the plate and at least one saddle member coupled to the plate. Alternatively, the occipital rod can be secured to the occipital bone.

96 Claims, 30 Drawing Sheets

U.S. PATENT DOCUMENTS

| | | | |
|---|---|---|---|
| 5,476,464 A | | 12/1995 | Metz-Stavenhagen et al. |
| 5,498,262 A | | 3/1996 | Bryan |
| 5,498,263 A | | 3/1996 | DiNello et al. |
| 5,501,684 A | | 3/1996 | Schlapfer et al. |
| 5,520,690 A | | 5/1996 | Errico et al. |
| 5,527,314 A | | 6/1996 | Brumfield et al. |
| 5,531,746 A | | 7/1996 | Errico et al. |
| 5,545,164 A | | 8/1996 | Howland |
| 5,549,608 A | | 8/1996 | Errico et al. |
| 5,554,157 A | | 9/1996 | Errico et al. |
| 5,562,661 A | | 10/1996 | Yoshimi et al. |
| 5,575,792 A | | 11/1996 | Errico et al. |
| 5,578,033 A | | 11/1996 | Errico et al. |
| 5,584,834 A | | 12/1996 | Errico et al. |
| 5,586,984 A | | 12/1996 | Errico et al. |
| 5,591,165 A | | 1/1997 | Jackson |
| 5,601,552 A | | 2/1997 | Cotrel |
| 5,601,553 A | | 2/1997 | Trebing et al. |
| 5,607,426 A | | 3/1997 | Ralph et al. |
| 5,609,593 A | | 3/1997 | Errico et al. |
| 5,609,594 A | | 3/1997 | Errico et al. |
| 5,643,265 A | | 7/1997 | Errico et al. |
| 5,647,873 A | | 7/1997 | Errico et al. |
| 5,669,910 A | | 9/1997 | Korhonen et al. |
| 5,669,911 A | | 9/1997 | Errico et al. |
| 5,672,176 A | * | 9/1997 | Biedermann et al. .......... 606/61 |
| 5,688,272 A | | 11/1997 | Montague et al. |
| 5,688,273 A | | 11/1997 | Errico et al. |
| 5,690,630 A | * | 11/1997 | Errico et al. ................... 606/61 |
| 5,716,355 A | | 2/1998 | Jackson et al. |
| 5,725,588 A | | 3/1998 | Errico et al. |
| 5,733,286 A | | 3/1998 | Errico et al. |
| 5,810,818 A | * | 9/1998 | Errico et al. ................... 606/61 |
| 5,817,094 A | | 10/1998 | Errico et al. |
| 5,876,402 A | | 3/1999 | Errico et al. |
| 5,879,351 A | | 3/1999 | Viart |
| 5,885,286 A | * | 3/1999 | Sherman et al. .............. 606/61 |
| 5,947,966 A | | 9/1999 | Drewry et al. |
| 5,980,523 A | | 11/1999 | Jackson |
| 6,015,409 A | | 1/2000 | Jackson |
| 6,080,156 A | | 6/2000 | Asher et al. |
| 6,113,600 A | | 9/2000 | Drummond et al. |
| 6,280,442 B1 | * | 8/2001 | Barker et al. .................. 606/60 |
| 2001/0001119 A1 | | 5/2001 | Lombardo |

* cited by examiner

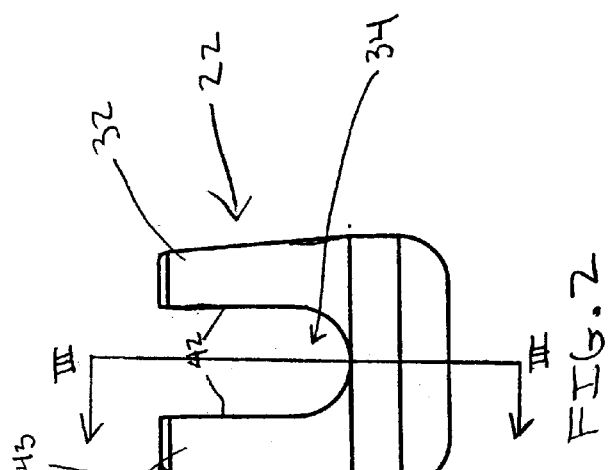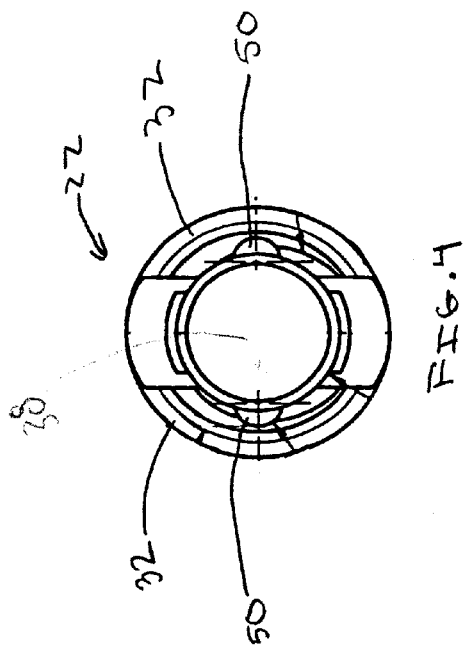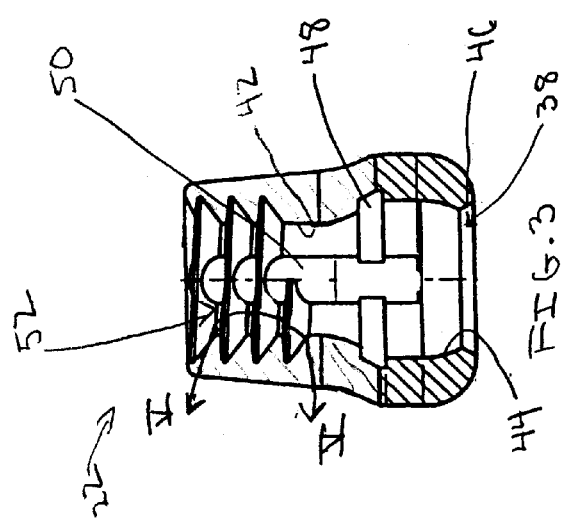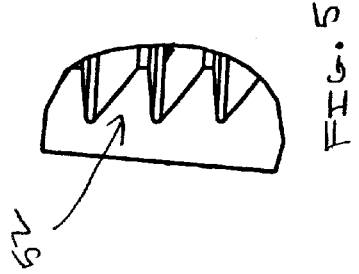

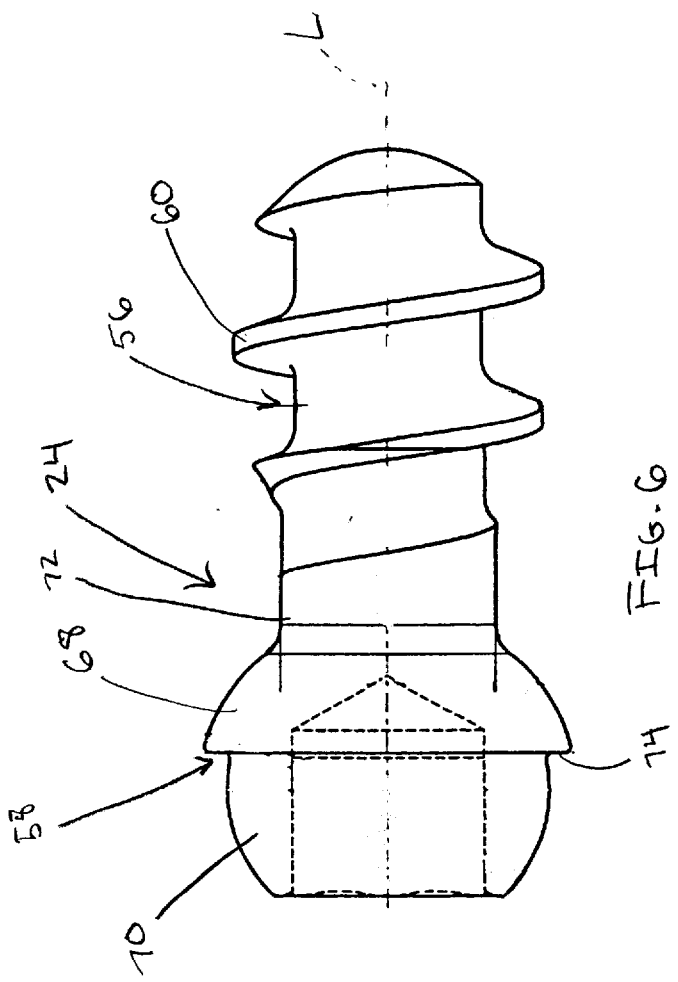
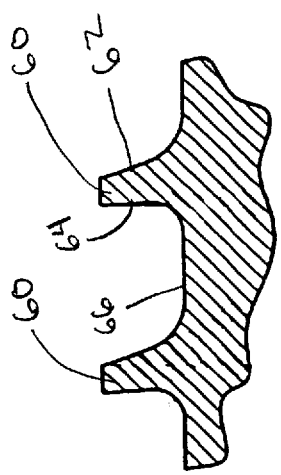
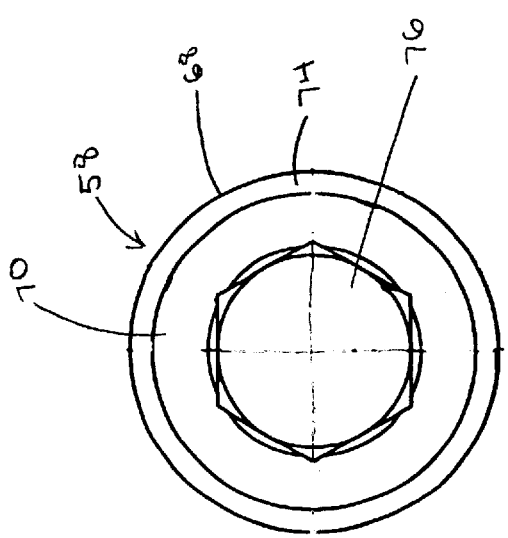

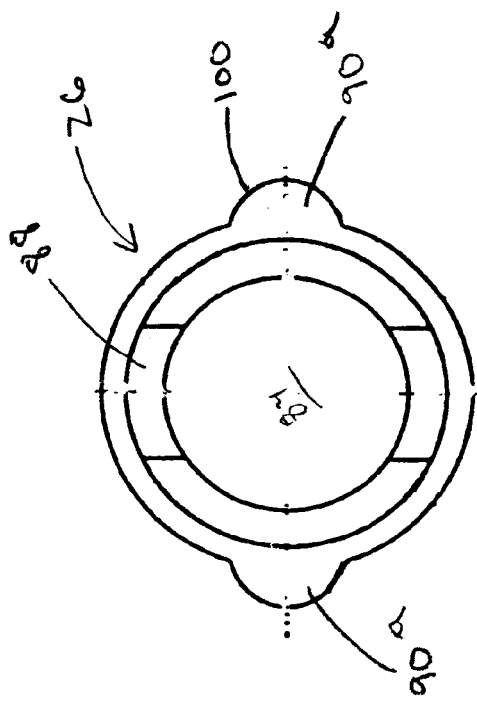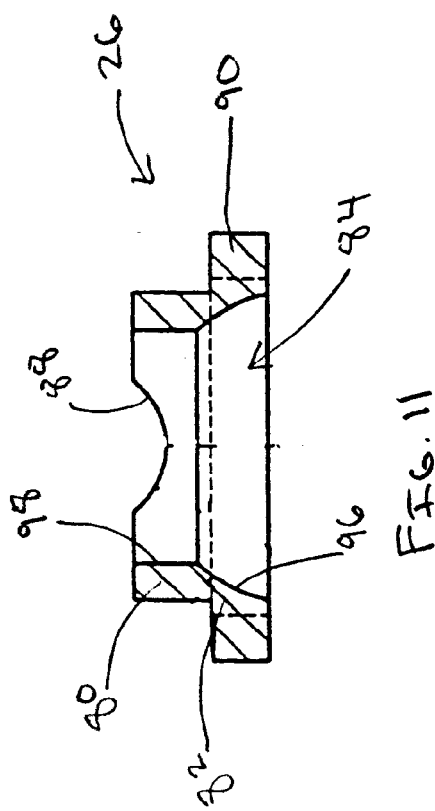

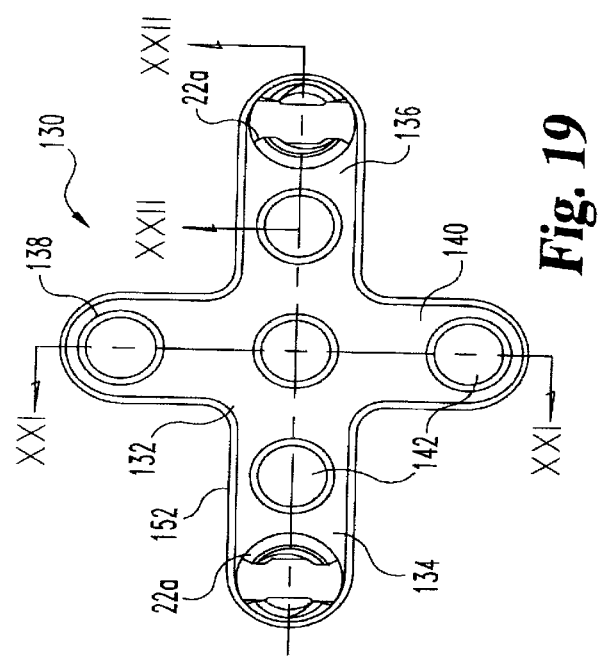
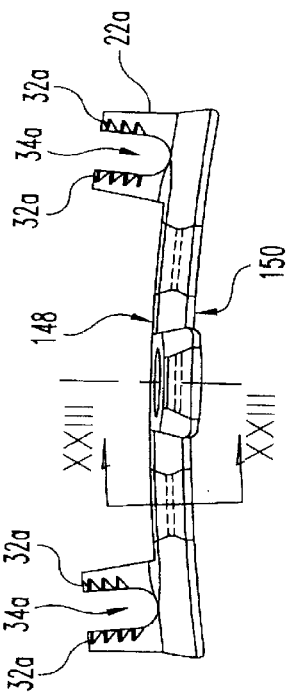
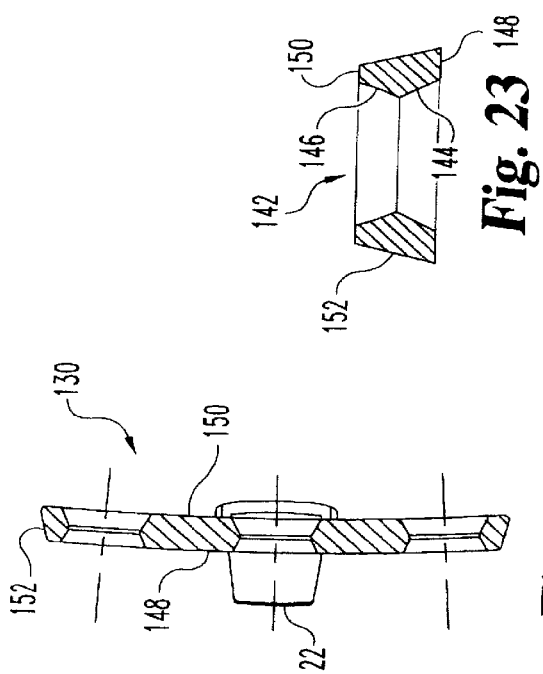
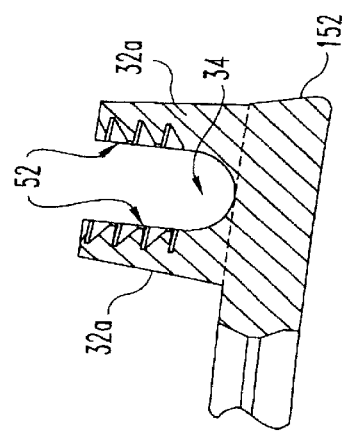
Fig. 19
Fig. 20
Fig. 23
Fig. 21
Fig. 22

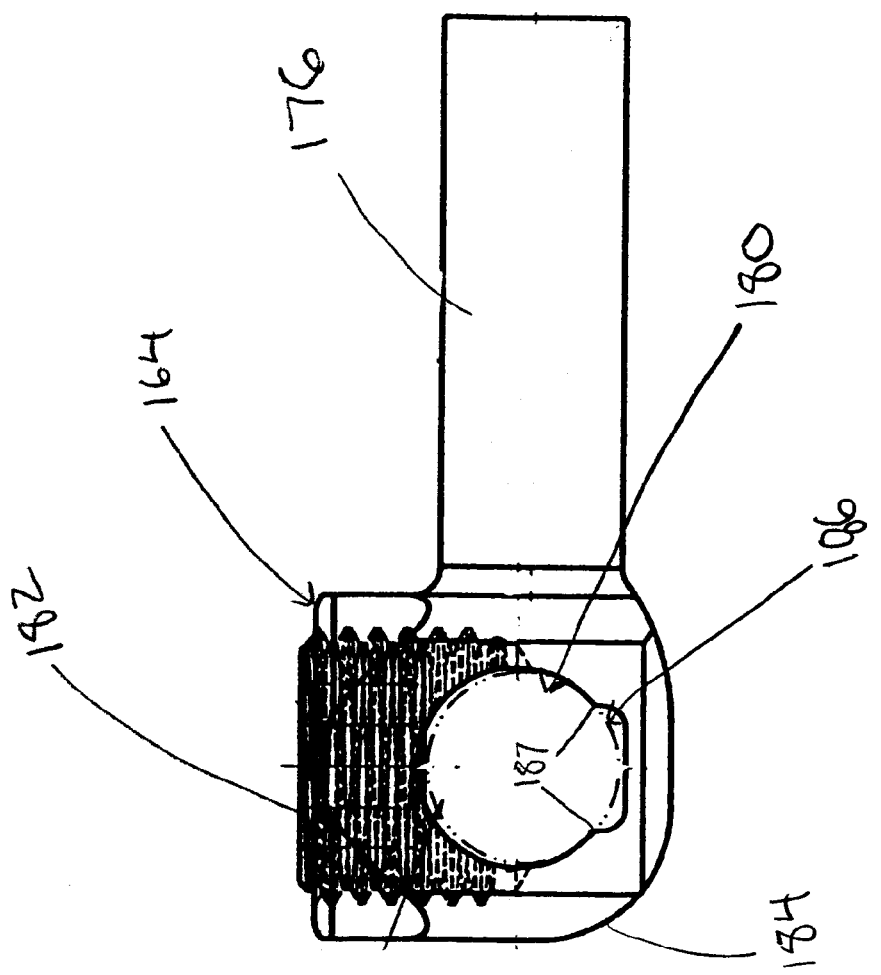

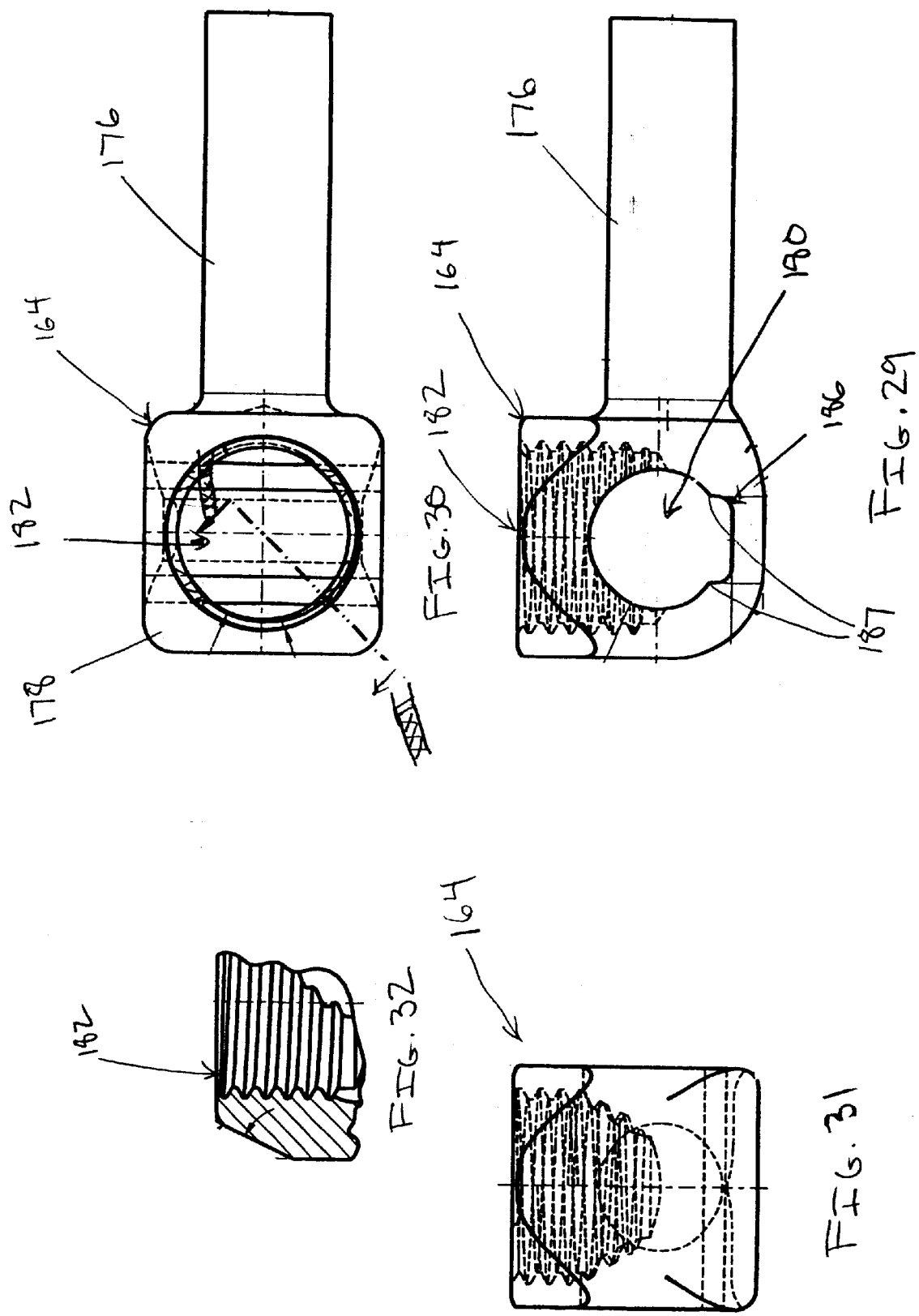

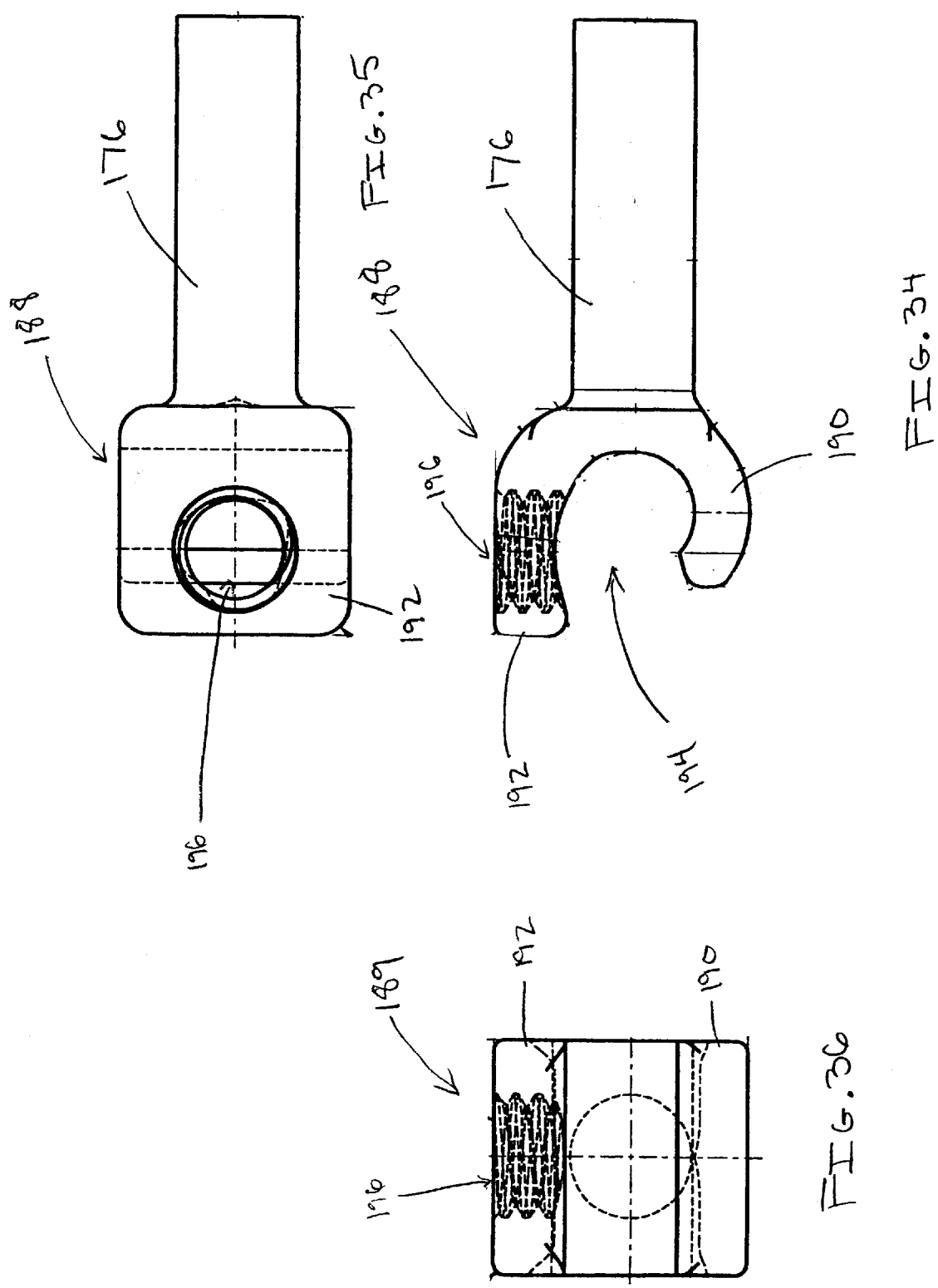

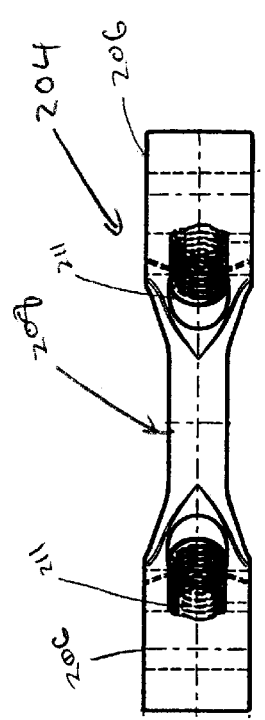
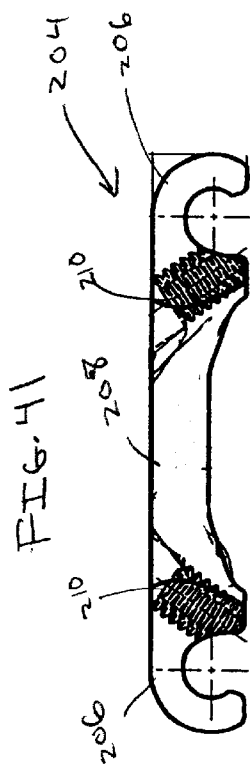
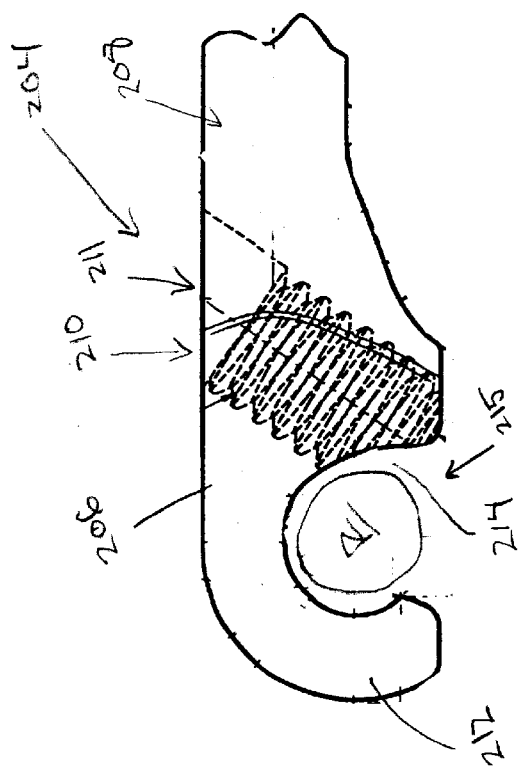

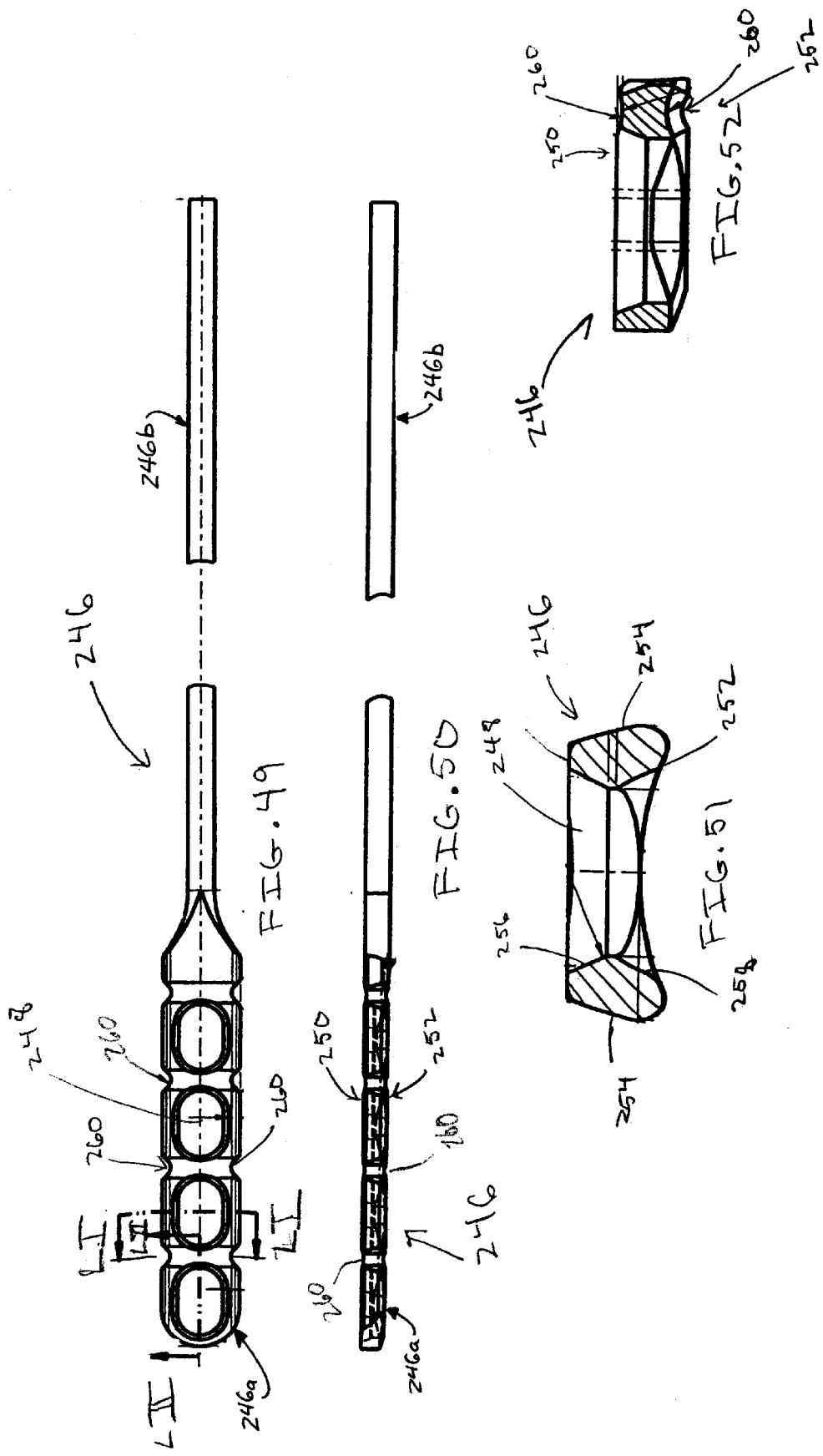

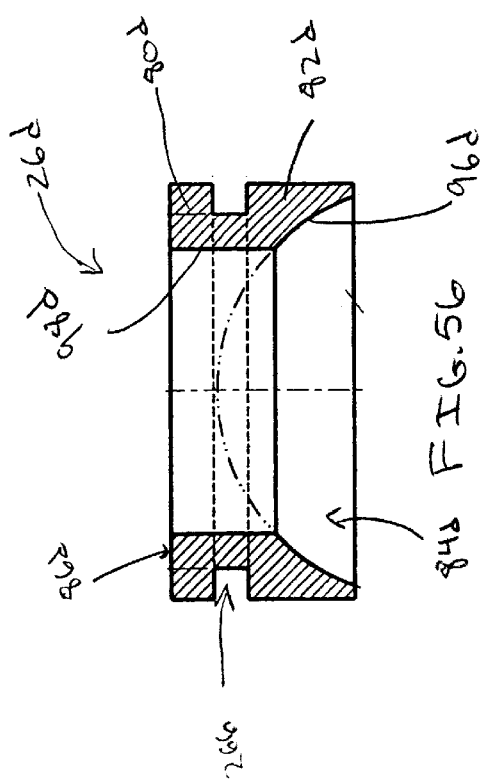
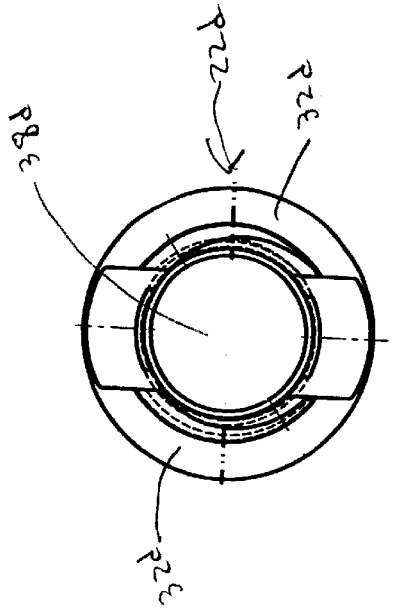
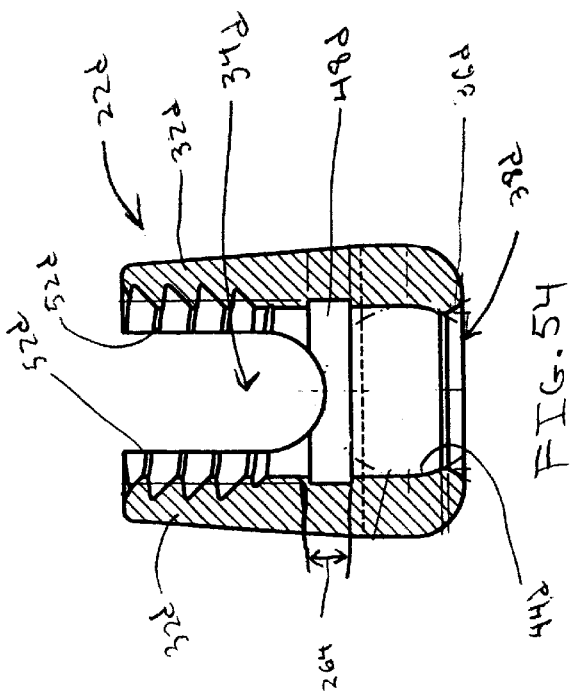

POSTERIOR FIXATION SYSTEM

BACKGROUND OF THE INVENTION

The present invention generally relates to orthopedic implants used for correction of spinal injuries or deformities, and more specifically, but not exclusively, concerns apparatuses for fixing a portion of the spine, such as the cervical spine, to allow correction or healing thereof.

In the realm of orthopedic surgery, it is well known to use implants to fix the position of bones. In this way, the healing of a broken bone can be promoted, and malformations or other injuries can be corrected. For example, in the field of spinal surgery, it is well known to place such implants into vertebrae for a number of reasons, including (a) correcting an abnormal curvature of the spine, including a scoliotic curvature, (b) to maintain appropriate spacing and provide support to broken or otherwise injured vertebrae, and (c) perform other therapies on the spinal column.

Typical implant systems include several pieces, which commonly are useful and may be associated with only specific other pieces. Bone screws, hooks, and clamps are well know as fixation devices, which are connected or adjoined to a particular bone as a connection between the remainder of the implant and the bone. Specially formed plates or rods are commonly used as stabilization and support members. Thus, in a common spinal implant system, a spinal plate is implanted along one or more vertebrae by driving a bone screw through the plate and into each of two vertebrae. The vertebrae are thus supported and kept in a particular position by the plate, so as to promote healing. One example of such an instrumentation system is U.S. Pat. No. 5,735,853 to Olerud.

Alternatively, a rod can be used as the support and stabilizing member. In such an implant, a series of two or more screws are inserted into two or more vertebrae to be instrumented. A rod is then placed within or coupled to the heads of the screws, or is placed within a connecting device that links the rod and a screw head, and the connections are tightened. In this way, a rigid supporting structure is fixed to the vertebrae, with the rod providing the support that promotes correction of the vertebral malformation or injury.

Many varieties of bone fixation devices (e.g. screws and hooks) are monoaxial in construction. That is, such devices are connected to the rod or plate such that a longitudinal axis through the rod or plate and a longitudinal axis through the fixation device are capable of only a single position with respect to each other. While useful in certain circumstances, in many therapeutic situations the degree of precision required to use such an inflexible device is impractical, or can lead to a longer duration of surgery, potentially awkward angles for the surgeon and for the patient, with the potential for attendant complications such as pain and/or extended rehabilitation.

More recently, bone fixation devices having multi-axial capability have been introduced. Examples of such constructs are shown in U.S. Pat. Nos. 5,797,911, 5,954,725, and 5,810,818. These devices help to reduce the required precision of placement of the fixation device, since a head portion of the fixation device is multi-axially positionable around the bone-threaded or hook portion. The head can thus be positioned so as to easily receive the rod, limiting or removing much of the positioning difficulty inherent in prior devices.

Most such devices are designed for spinal fixation at the thoracic and lumbar levels. Accordingly, there is a need in the art for a comprehensive multi-axial spinal implant system, and particularly one that is useful in the cervical region of the spine.

SUMMARY OF THE INVENTION

One form of the present invention is a unique multi-axial bone attachment assembly. Other forms concern a unique spinal implant system, a unique orthopedic fixation plate, a unique cross-link connector, and another unique multi-axial bone attachment assembly.

A further form of the present invention is directed to a unique multi-axial bone attachment assembly that includes a saddle member, a bone anchoring member, and a washer (crown member). The saddle member has a plurality of upright portions that define a channel through the saddle member. The saddle member further has a hole therethrough bounded by an inner wall, and the hole forms a lower opening in the saddle member. The bone-anchoring member extends through the opening. The bone-anchoring member includes a head portion and an anchoring portion. The washer has a recessed portion for accommodating an orthopedic rod and may include a radially extending projection. The washer is fitted within the hole of the saddle member and atop the bone-anchoring member.

Yet another form concerns a unique spinal implant system. A saddle member has a plurality of upright portions that define a channel through the saddle member. The saddle member further has a transverse hole defined through the upright portions that is transverse with respect to the channel. A bone-anchoring member is coupled to the saddle member for anchoring the saddle member to bone. An offset member is adapted to couple to an orthopedic rod, and the offset member has a coupling member and a body adapted to couple to the rod. The coupling member extends from the body and through the transverse hole of the upright members.

Another form is directed to a unique cross-shaped orthopedic plate. The plate includes a cross-shaped member. The cross-shaped member has a longitudinal axis connecting first and second longitudinal ends and a transverse axis connecting first and second transverse ends. The cross-shaped member has a plurality of apertures therethrough. At least one saddle member is attached to the cross-shaped member, and the saddle member has a plurality of upright portions that define a channel through the saddle member.

A further form concerns a unique cross-link connector. The connector includes a plurality of coupling ends each adapted to couple to an orthopedic rod. A cylindrical member is integrally connected to the coupling ends. The cylindrical member has a cylindrical shape for permitting multi-axial bending of the cylindrical member.

Still yet another form is directed to a unique multi-axial bone attachment assembly. A saddle member has a plurality of upright portions that define a channel through the saddle member. The saddle member further has a hole therethrough bounded by an inner wall, and the hole forms a lower opening in the saddle member. A bone-anchoring member extends through the opening. The bone-anchoring member includes a coupling portion provided in the hole for permitting multi-axial movement of the anchoring member and an anchoring portion. An expansion member is coupled to the anchoring member for expanding the coupling portion in order to lock the anchoring member into position.

The present invention provides a modular fixation system that allows a surgeon multiple treatment options for patients, allowing the surgeon to adapt the treatment to specific patient anatomy. The concepts surrounding the present invention are specifically designed for cervical vertebral fixation, but could be extended to include thoracic, lumbar and sacral fixation. Other advantages and objects of the present invention will be evident in view of the following specification and drawings.

BRIEF DESCRIPTION OF THE DRAWINGS

FIG. 2 shows a side view of a saddle member according to the embodiment shown in FIG. 1.

FIG. 3 shows a cross-sectional view of the saddle member taken along line III—III in FIG. 2.

FIG. 4 shows a top view of the saddle member of FIG. 2.

FIG. 5 shows an enlarged cross-sectional view of the saddle member taken along line V—V in FIG. 3.

FIG. 19 shows a top view of an orthopedic plate according to one embodiment.

FIG. 20 shows a side view of the orthopedic plate of FIG. 19.

FIG. 21 shows a cross-sectional view of the orthopedic plate taken along line XXI—XXI in FIG. 19.

FIG. 22 shows a cross-sectional view of a portion of the orthopedic plate taken along line XXII—XXII in FIG. 19.

FIG. 23 shows a cross-sectional view of a portion of the orthopedic plate taken along line XXIII—XXIII in FIG. 20.

FIG. 29 shows a side view of the offset member of FIG. 28.

FIG. 30 shows a top view of the offset member of FIG. 28.

FIG. 31 shows an end view of the offset member of FIG. 28.

FIG. 32 shows a cross-sectional view of the offset member of FIG. 28.

FIG. 34 shows a cross-sectional view of the offset member of FIG. 33.

FIG. 35 shows a top view of the offset member of FIG. 33.

FIG. 36 shows an end view of the offset member of FIG. 33.

DESCRIPTION OF THE PREFERRED EMBODIMENTS

Figure 1:
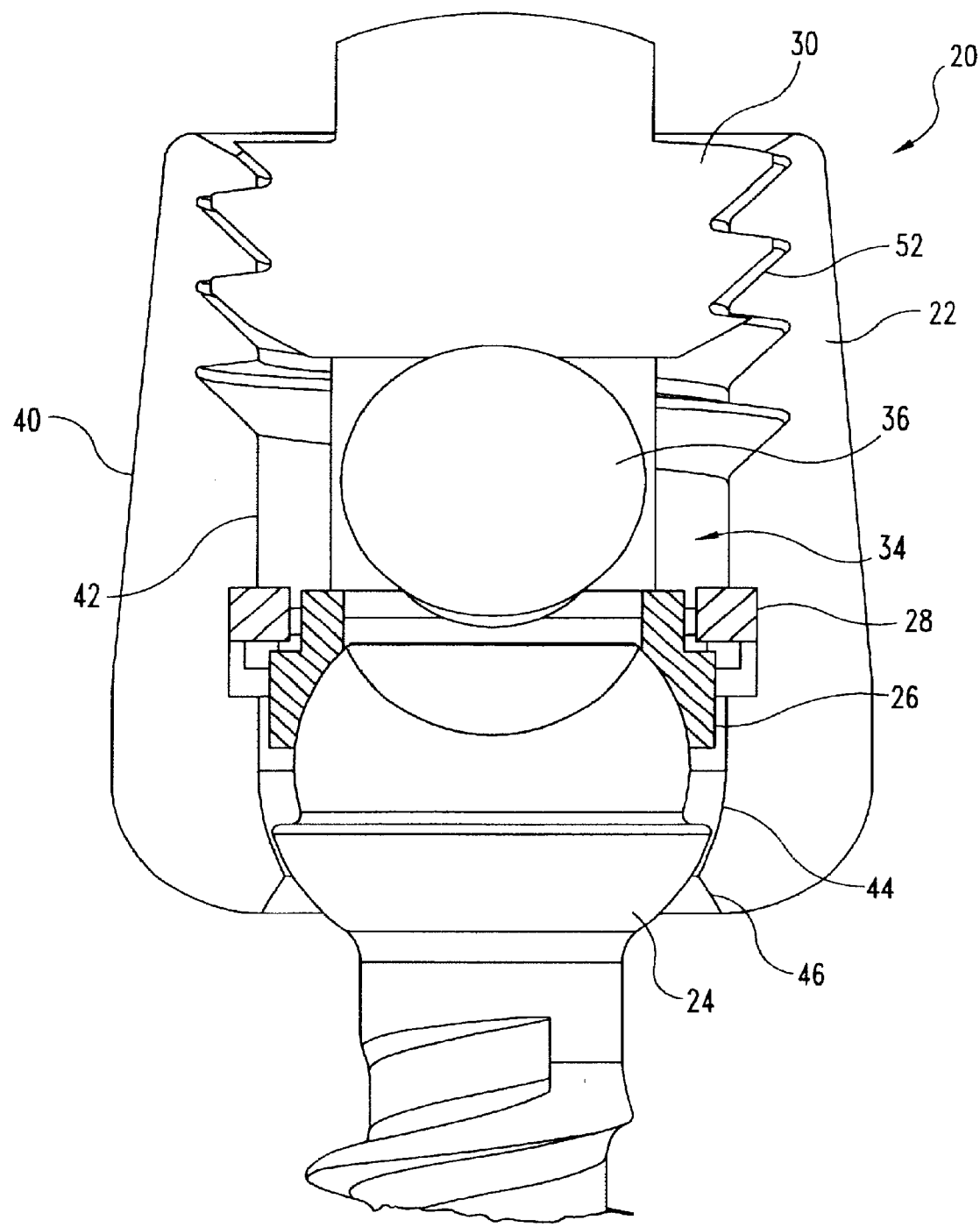
FIG. 1 shows a partial cross-sectional view of a bone anchor assembly according to one embodiment of the present invention.

For the purpose of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein, being contemplated as would normally occur to one skilled in the art to which the invention relates.

In FIG. 1, there is shown an embodiment of a multi-axial bone anchor assembly 20 according to the present invention. Bone anchor assembly 20 includes a saddle member 22, a bone anchoring member 24, and a washer (crown member) 26. In some embodiments, assembly 20 will further include a C-shaped snap ring 28 and a set screw 30, which are fitted with saddle member 22 as will be described hereafter.

As shown in FIGS. 1–4, saddle member 22 generally has a U-shape, with two upright portions 32 defining a channel 34 extending through saddle member 22. Channel 34 is then configured to accommodate an elongated member 36, such as a spinal rod. For posterior cervical fixation, rod 36 may have one of a number of desired lengths. As seen in FIG. 1, the width of channel 34 is slightly larger than the diameter of rod 36, which allows easier insertion of rod 36 into channel 34, also allows for compensation for contouring of the rod, and allows use of a range of rod sizes with the same saddle member 22. Saddle member 22 further includes a hole 38 therethrough, hole 38 being in one particular embodiment substantially perpendicular to channel 34 and substantially parallel to upright portions 32.

In a particular embodiment of saddle member 22, illustrated in FIGS. 2–5, upright portions 32 each have an outer surface 40 and an inner surface 42. Inner surfaces 42 are parallel to hole 38, along a longitudinal axis of saddle member 22. Outer surfaces 40 are angled with respect to inner surfaces 42 and the longitudinal axis of saddle member 22. In one specific embodiment, outer surfaces 40 have an inward taper 43, which taper allows for easier handling of the saddle member 22 and reduced bulk of saddle member 22. Near the bottom of saddle member 22, hole 38 is narrowed by a wall portion 44. Below wall portion 44, hole 38 opens outward by virtue of a conical wall portion 46. Conical wall portion 46 allows bone anchor member 24 to be positioned in any of an infinite number of angular positions relative to saddle member 22 by reducing interference of the lower portion of saddle member 22 with a shank portion of bone anchor member 24.

The illustrated embodiment of saddle member 22 further includes an inner groove 48 that extends around hole 38. Groove 48 is configured to accommodate snap ring 28 in a compressed condition, i.e., the outer diameter of groove 48 is at least slightly smaller than the normal uncompressed outer diameter of snap ring 28. The illustrated embodiment of saddle assembly 22 further includes a trough 50 extending longitudinally within each of upright portions 32. Trough 50 accommodates placement of washer 26, as further described below, and may have a rounded (e.g. cylindrical), squared, or other appropriate shape to accommodate washer 26. Upright portions 32 further include an internally threaded portion 52, as shown in FIGS. 1 and 3. Internally threaded portions 52 are configured to be threadedly coupled with set screw 30, as described hereafter.

Figure 6A:
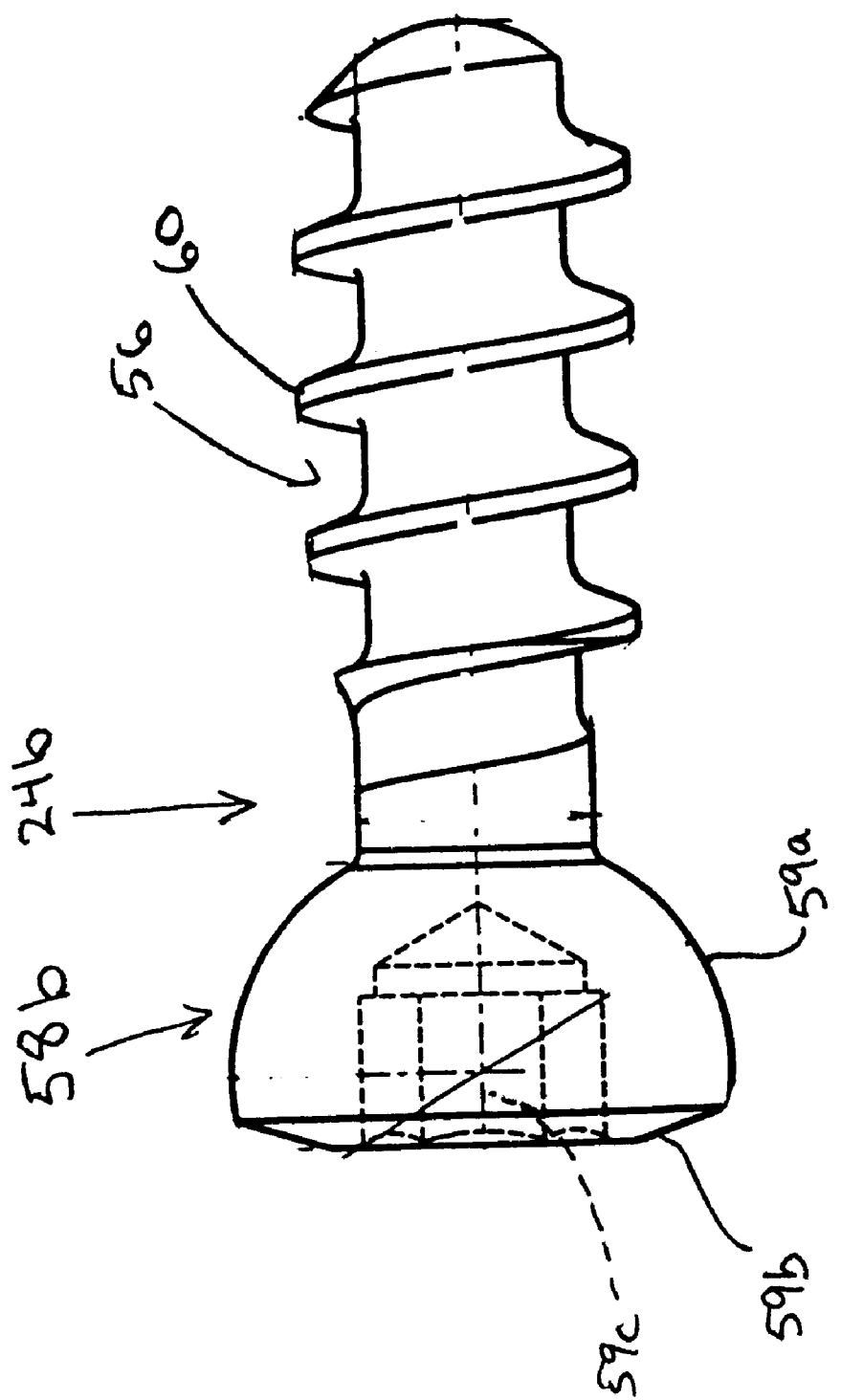
FIG. 6a shows a side view of an anchor member according to another embodiment.
Figure 6:
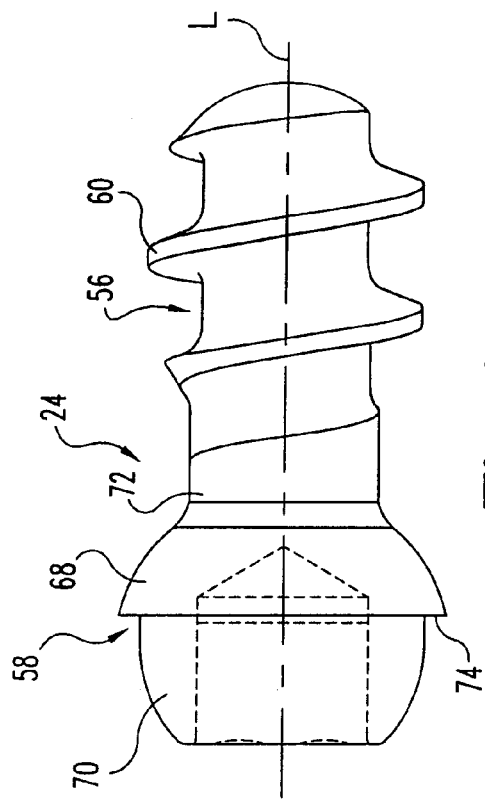
FIG. 6 shows a side view of an anchor member according to one embodiment.
Figure 7:
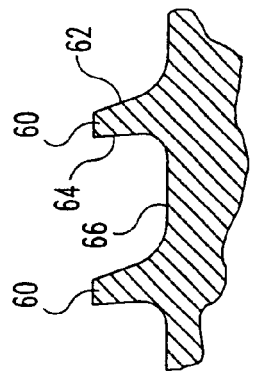
FIG. 7 shows an enlarged cross-sectional view of threads of the embodiment of the anchor member shown in FIG. 6.
Figure 8:
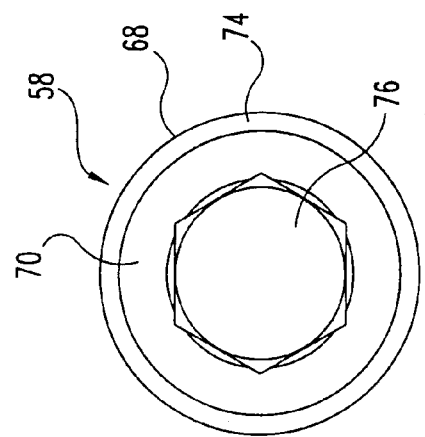
FIG. 8 shows a top view of the anchor member of FIG. 6.
Figure 6A:
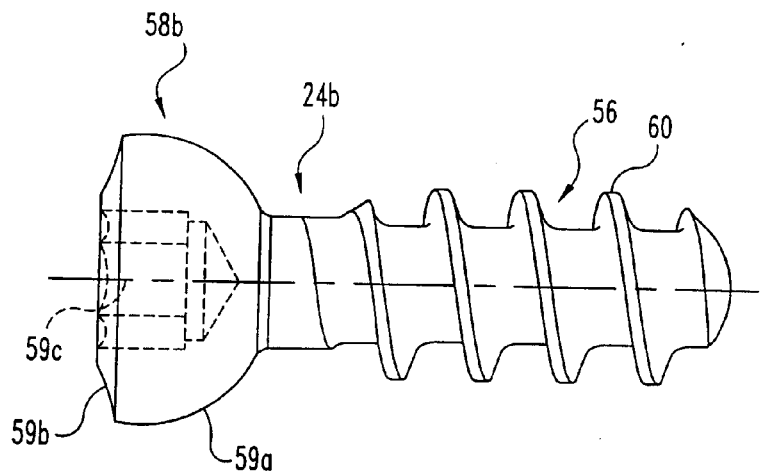
Figure 9:
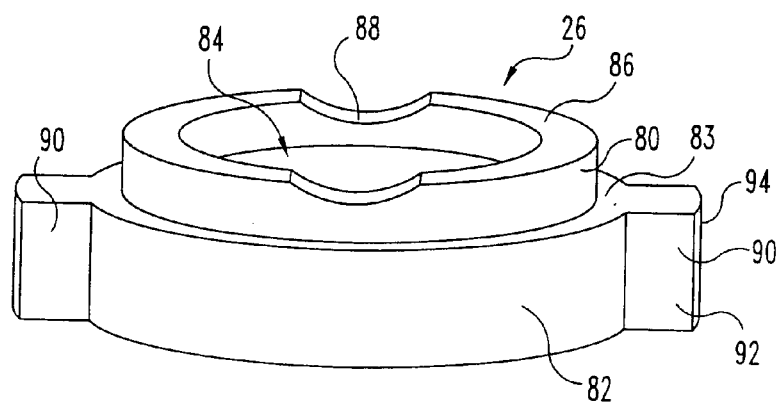
Figure 10:
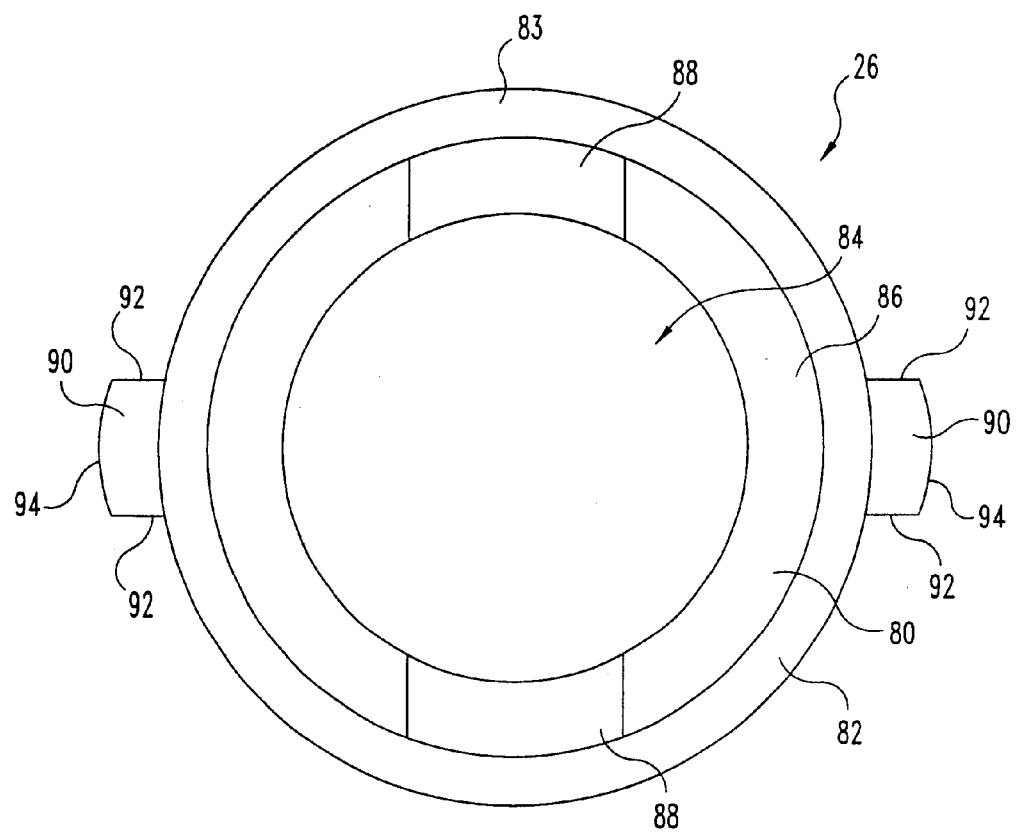

As shown in FIGS. 6–8, one embodiment of the bone anchor member 24 of the present invention has a threaded portion 56 and a head portion 58. In a specific embodiment, threaded portion 56 includes a thread 60 having a forward or leading flank 62 and a rearward or load flank 64 and a root surface 66, in which load flank 64 and root surface 66 form an acute angle. Such an acute angle between load flank 64 and root surface 66 may be termed a "reverse angle" thread.

Head portion 58 of bone anchor member 24 includes a lower head portion 68 and an upper head portion 70. Lower head portion 68 is generally convex, and in one embodiment forms part of a sphere. In the illustrated embodiment, the lower head portion 68 extends from a shank portion 72 in a direction away from threaded portion 56, and stops at/or before a tangent to lower head portion 68 would be parallel to a longitudinal axis L of bone anchor member 24. Upper head portion 70 is also generally convex, and forms a part of a sphere in the illustrated embodiment. Upper head portion 70 is diametrally smaller than lower head portion 68 and head portions 68 and 70 are connected by a lip 74. A tool-engaging recess 76 is formed in upper head portion 70, and may extend into lower head portion 68. In another embodiment shown in FIG. 53, head portion 58a of bone anchor member 24a does not have a lip 74.

Figure 9:
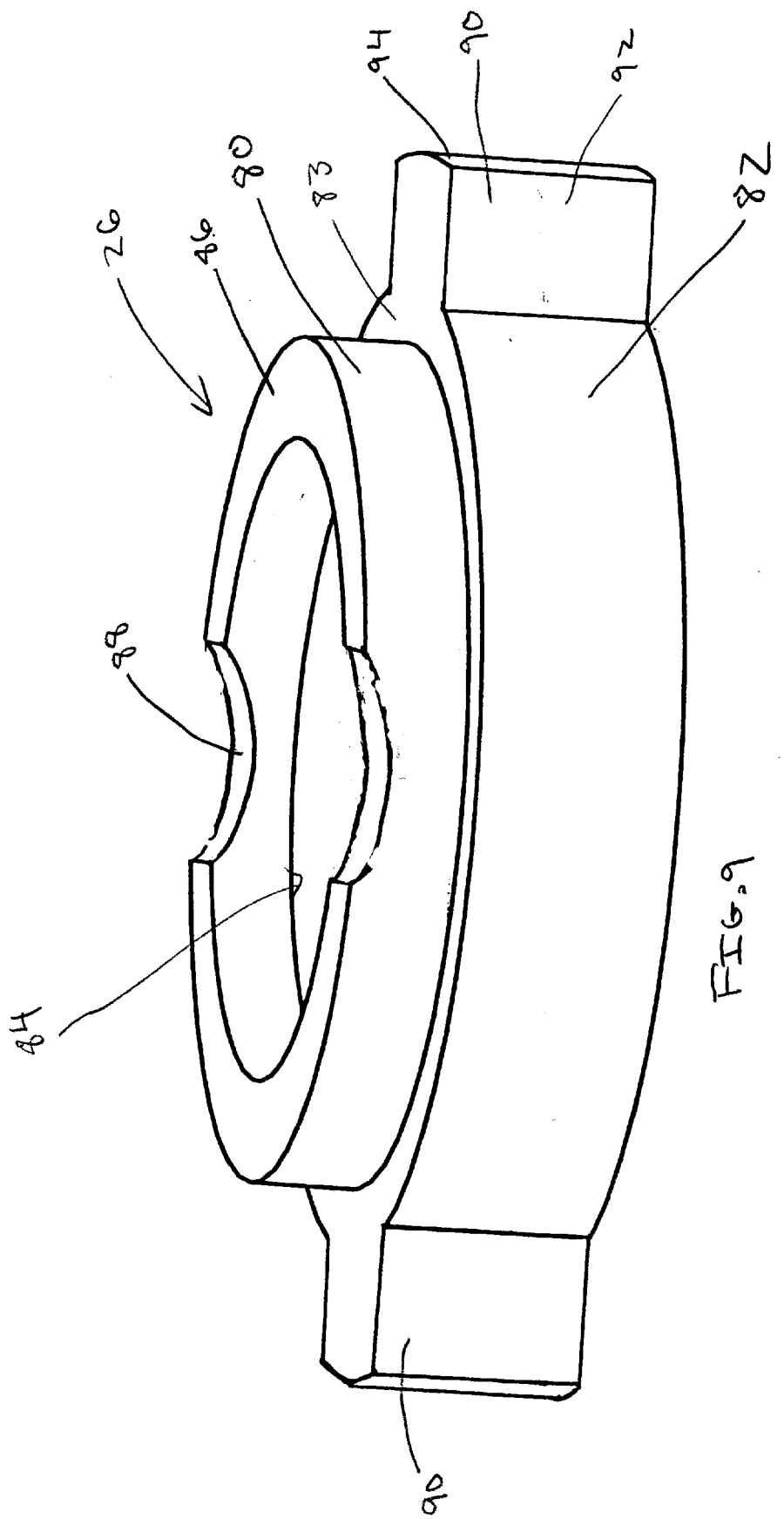
FIG. 9 shows a perspective view of a washer according to one embodiment of the present invention.
Figure 10:
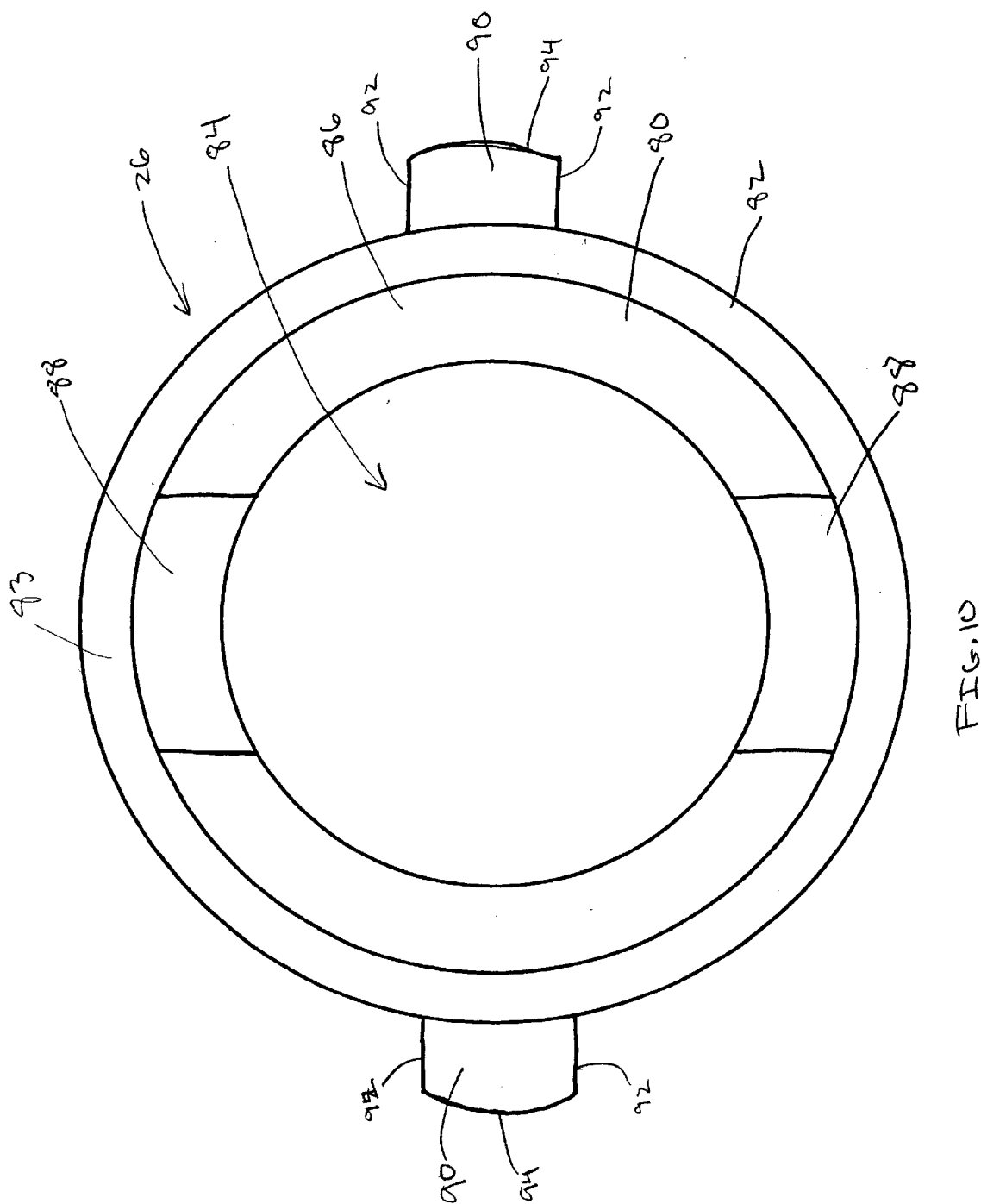
FIG. 10 shows a top view of the washer of FIG. 9.
Figure 11:
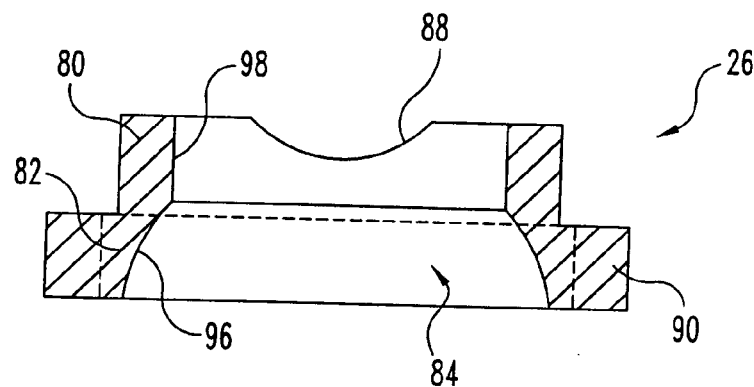
FIG. 11 shows a cross-sectional view of the washer of FIG. 9

Referring now to FIGS. 9–11, there is shown an embodiment of washer 26 of the present invention. Washer 26 includes an upper portion 80, a lower portion 82, and a hole 84 therethrough. Upper portion 80 and lower portion 82 may be constructed integrally or may be separately constructed and attached together in any known manner. An upper surface 86 of upper portion 80 includes recessed portions 88 in the illustrated embodiment, which recessed portions 88 form a part of a cylinder sized and configured to accommodate placement of an elongated member (such as rod 36 of FIG. 1) therein. Lower portion 82 further includes an upper surface 83 that faces snap ring 28.

Referring now to FIG. 11, washer 26 has a hole 84 provided through both upper portion 80 and lower portion 82. Hole 84 includes a lower concave surface 96 and a cylindrical surface 98. Concave surface 96 in one specific embodiment has a spherical shape so as to substantially coincide with a portion of upper head portion 70 of anchoring member 24. Lower portion 82 is generally in the shape of a circular disc, and includes two projections 90 extending radially therefrom. Projections 20 in conjunction with troughs 50 align recessed portions 88 of washer 26 with channel 34 and prevent rotation of washer 26 so as to minimize misalignment between rod 36 and recessed portions 88.

Figure 12:
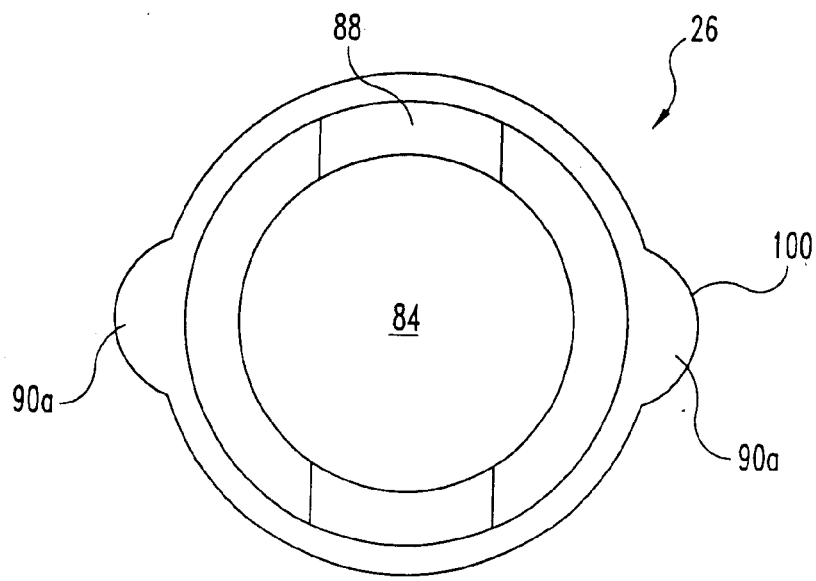
FIG. 12 shows a top view of another embodiment of a washer according to the present invention.
Figure 14:
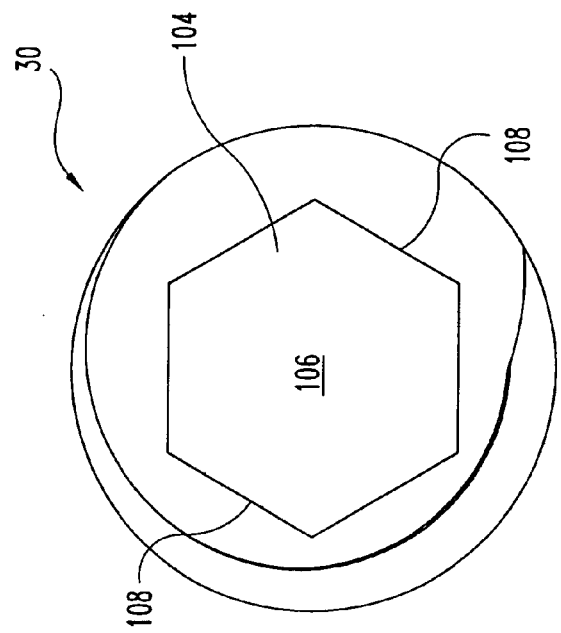
Figure 13:
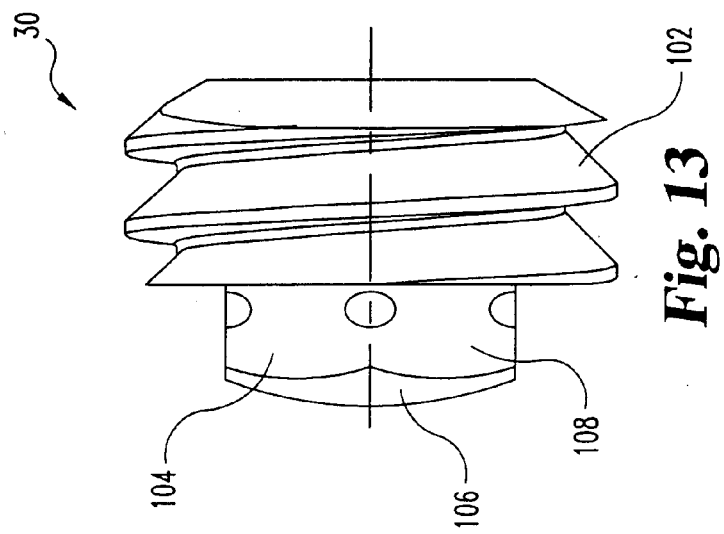
Figure 16:
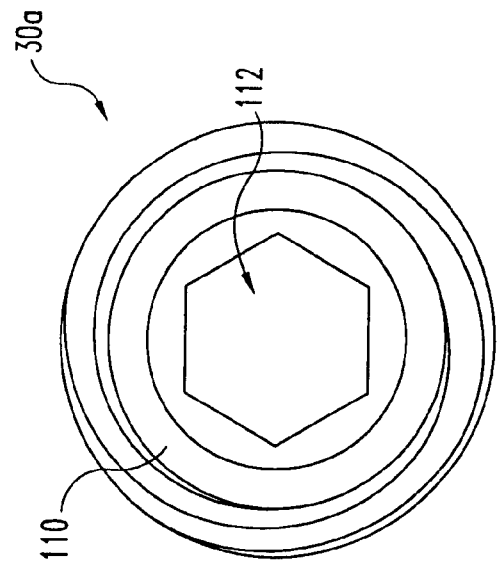
Figure 15:
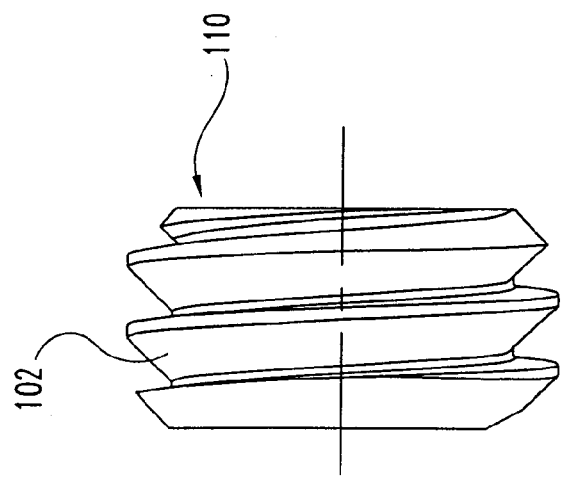
Figure 18:
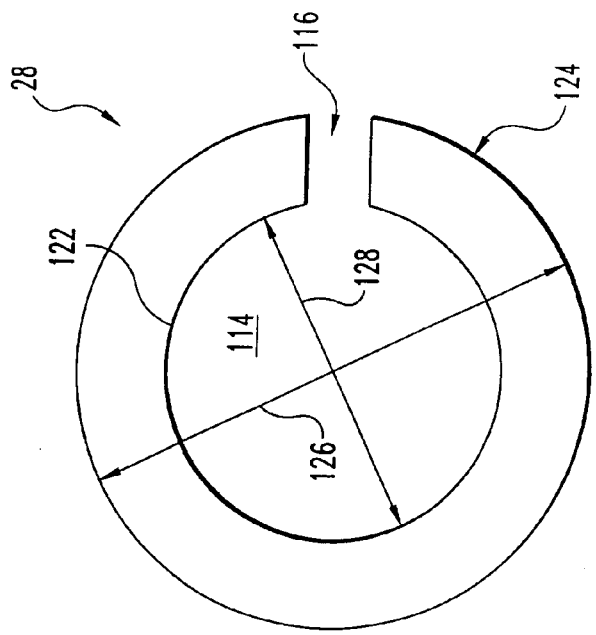
Figure 17:
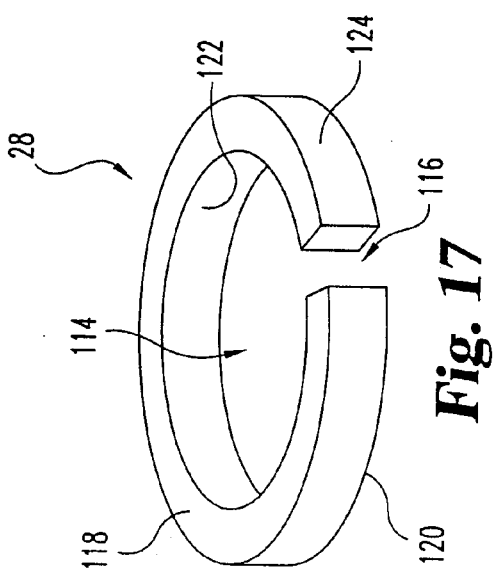
Figure 17A:
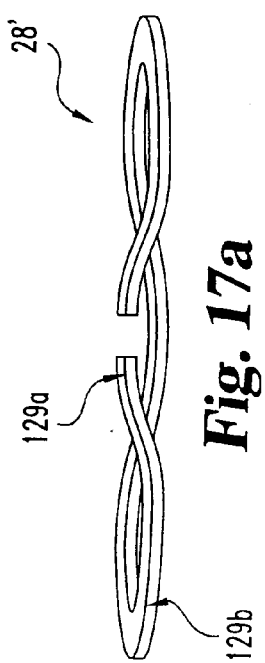
Figure 24:
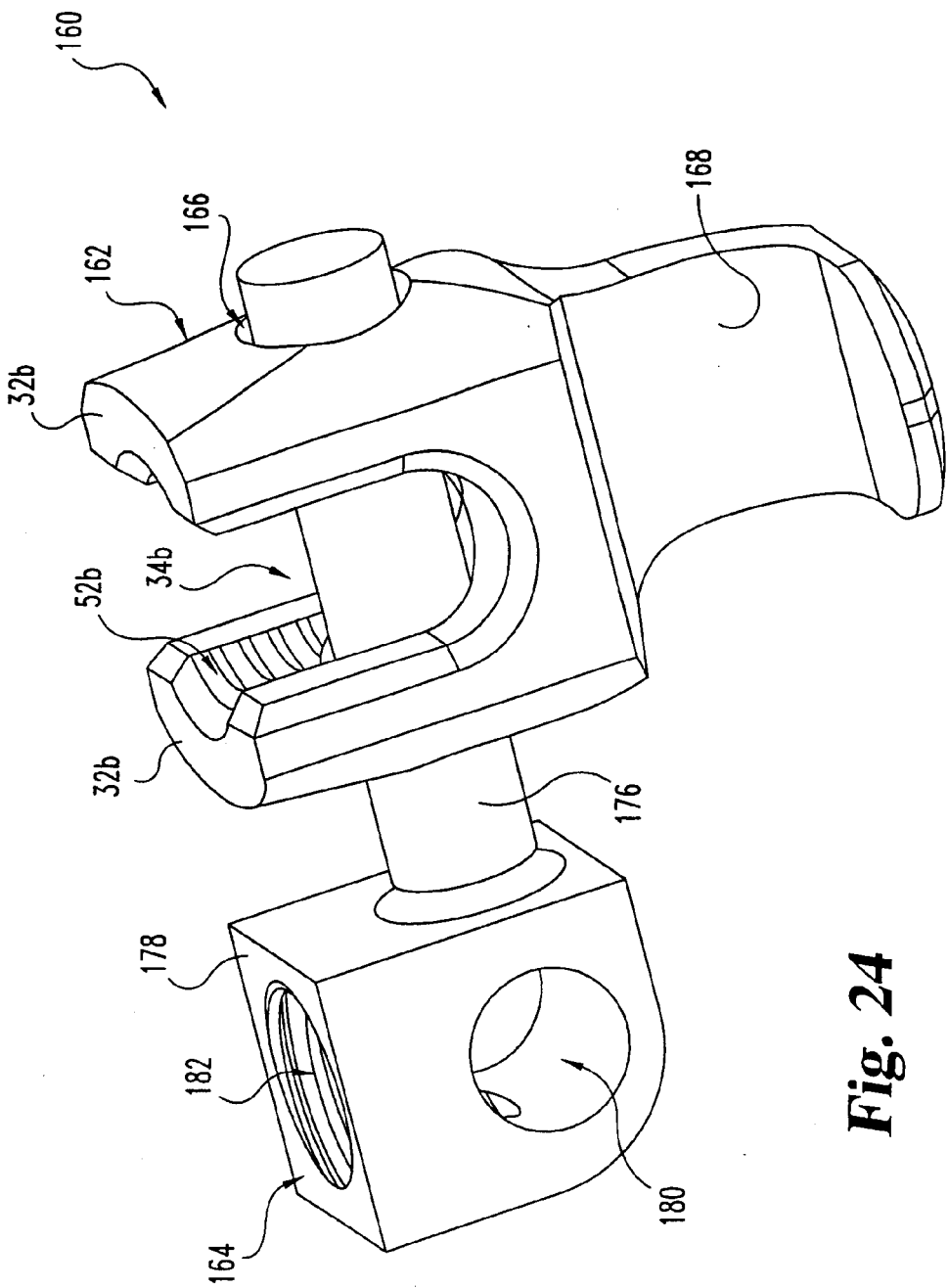
Figure 28:
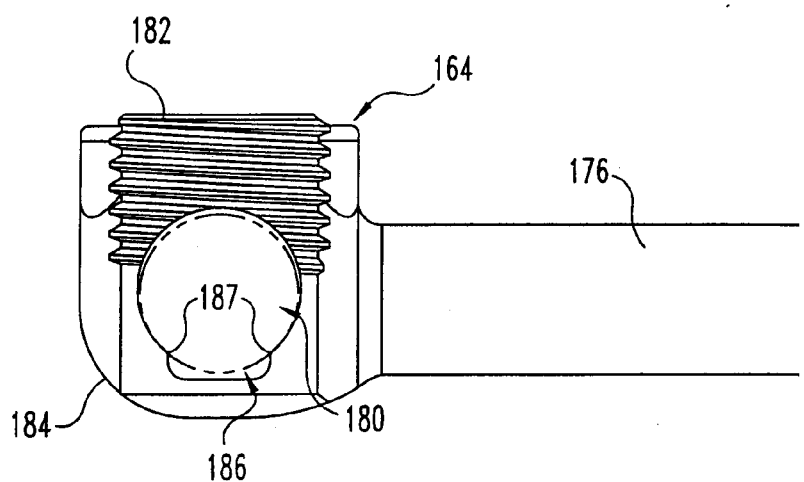
FIG. 28 shows a partial cross-sectional view of an offset member according to another embodiment of the present invention.
Figure 28A:
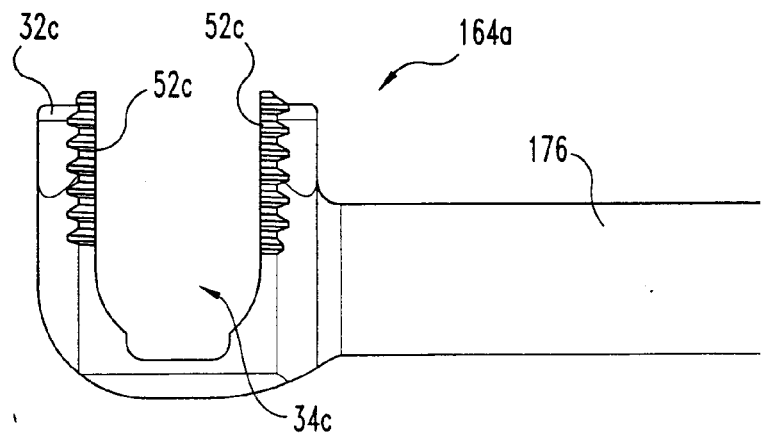
Figure 33:
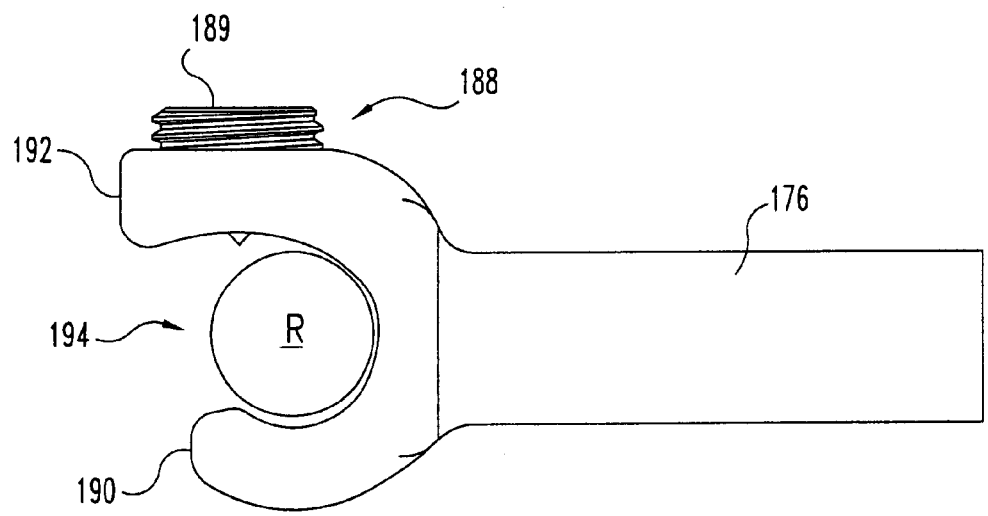
Figure 38:
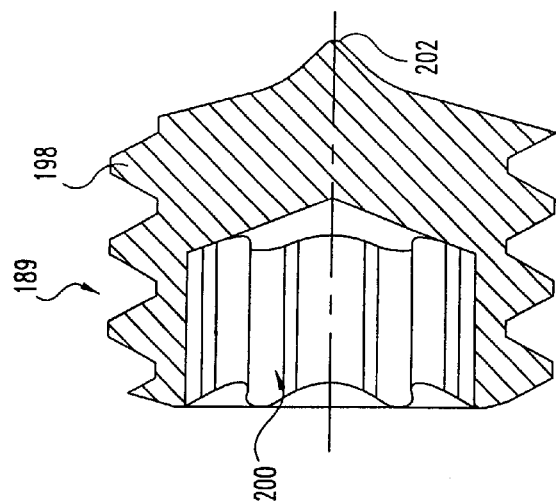
Figure 37:
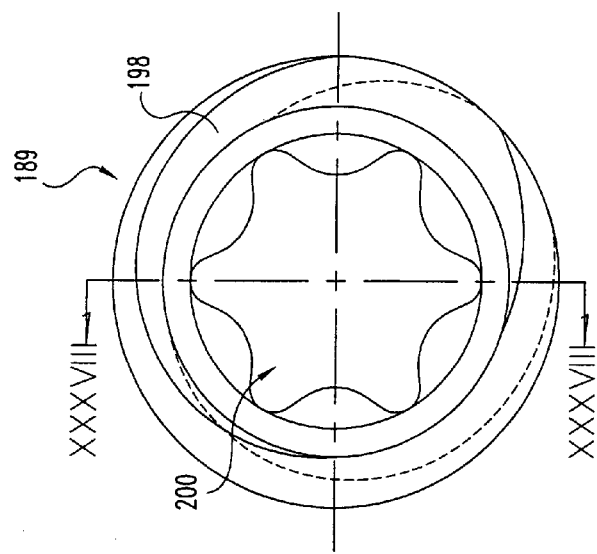
Figure 39:
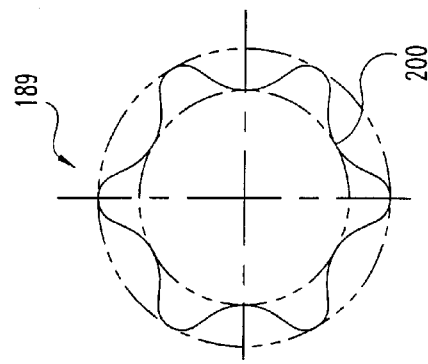

In one embodiment, shown in FIGS. 9–10, projections 90 each include two substantially planar side surfaces 92, and an end surface 94 that is rounded and may form a portion of a cylinder. Projections 90 are sized and shaped so as to fit and slide easily within the troughs 50 upright portions 32 of saddle member 22. In another embodiment illustrated in FIG. 12, projections 90a each include a rounded end surface 100.

Multi-axial bone anchor assembly 20 can further include a set screw 30. As illustrated in FIGS. 13–16, set screw 30 is generally cylindrical and has external threads 102. External threads 102, in one embodiment, are buttress threads. In another embodiment, threads 102 could be reverse angle threads so as to minimize splaying between the two upright members 32. An example of such reverse angle threading is disclosed in U.S. patent application Ser. No. 09/188,825, which is hereby incorporated by reference.

Figure 13:
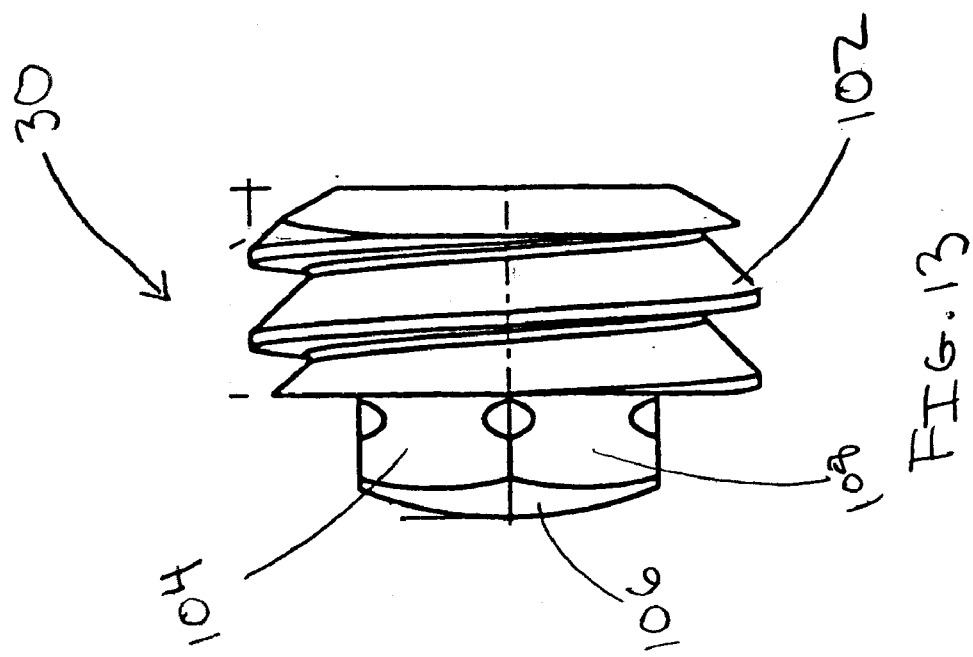
FIG. 13 shows a side view of a set screw according to one embodiment of the present invention.
Figure 14:
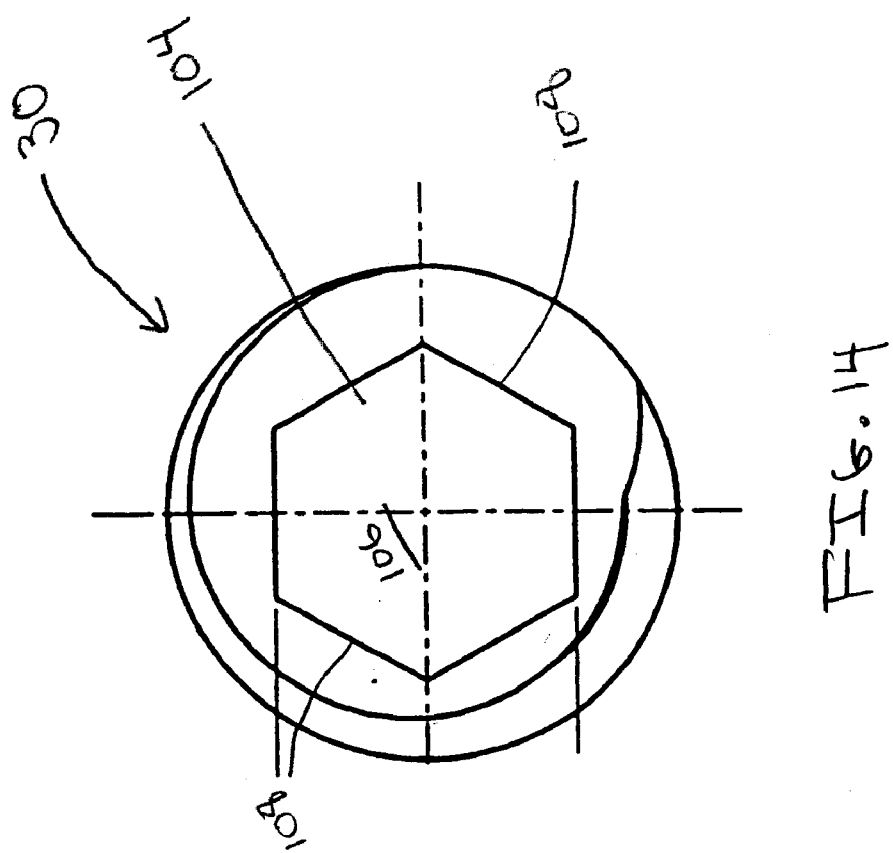
FIG. 14 shows a top view of the set screw of FIG. 13.
Figure 16:
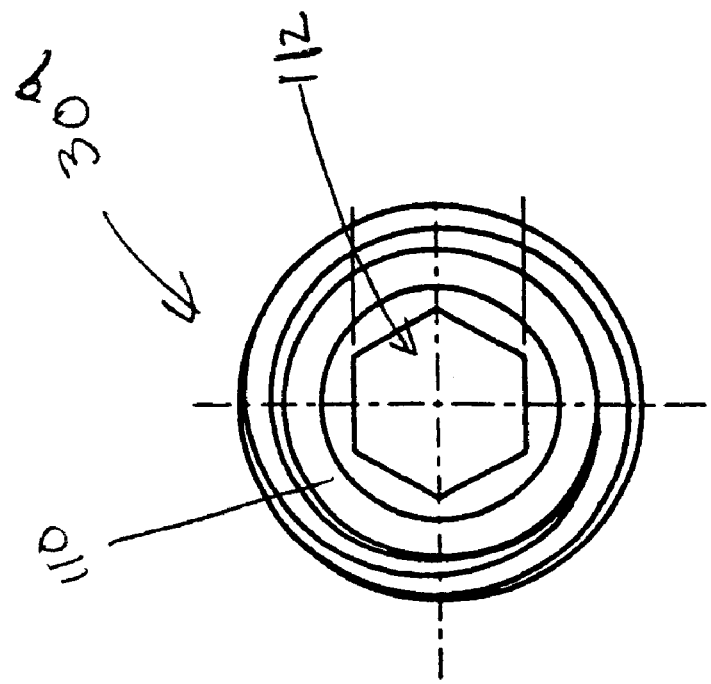
FIG. 16 shows a top view of the set screw of FIG. 15.
Figure 15:
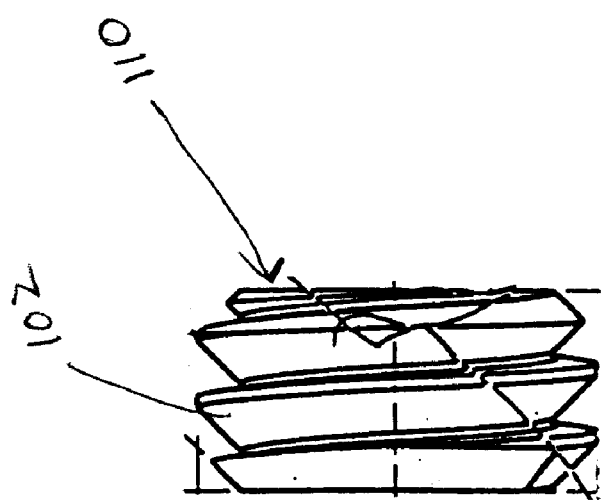
FIG. 15 shows a side view of a set screw according to another embodiment of the present invention.

Set screw 30, in the embodiment illustrated in FIGS. 13–14, has at one end a tool-engaging portion 104. Tool-engaging portion 104 has a rounded end surface 106 and substantially planar tool-engaging surfaces 108. Since end surface 106 is rounded, internal trauma to a patient can be reduced. Tool-engaging surfaces 108, in one embodiment, are oriented in a hexagonal configuration. Once set screw 30 is secured to saddle member 22, tool engaging portion 104 can be sheared off or otherwise removed so as to further reduce the profile of assembly 20. As illustrated in FIGS. 15–16, another embodiment of set screw 30a includes a substantially flat end surface 110 in order to minimize the profile of assembly 20. Set screw 30a further includes a tool-engaging bore 112. Tool-engaging bore 112 is used in conjunction with a tool for introducing set screw 30a into saddle member 22.

Figure 17:
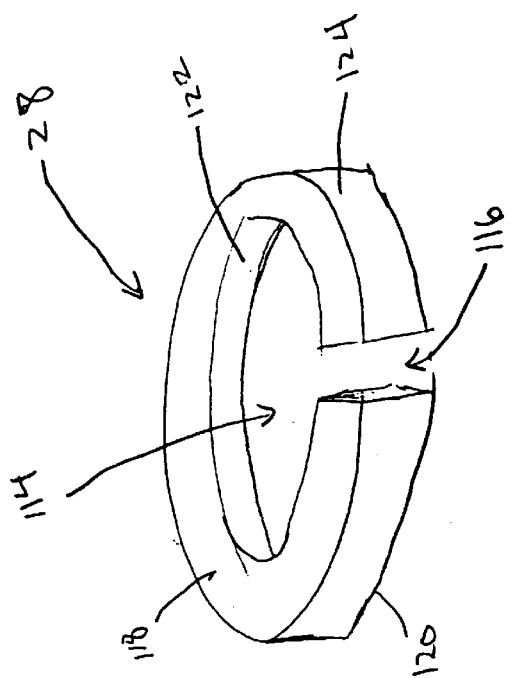
FIG. 17 shows a perspective view of a snap ring for use in the present invention.
Figure 18:
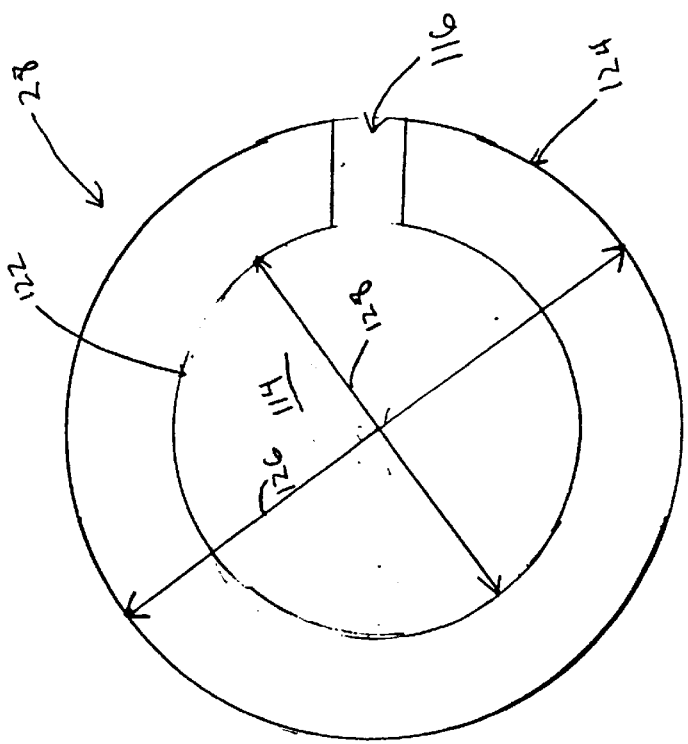
FIG. 18 shows a top view of the snap ring of FIG. 17.

In certain embodiments, multi-axial bone anchor assembly 20 includes snap ring 28 in order to secure washer 26 against anchoring member 24. One embodiment of such a snap ring 28 is shown in FIGS. 17–18. Snap ring 28 has a central opening 114 and a compression slot 116 defined therein. Snap ring 28 further has a first surface 118, an opposite second surface 120, an inner lateral surface 122 defining opening 114, and an outer lateral surface 124. Compression slot 116 allows snap ring 28 to compress and fit into inner groove 48 of saddle member 22. The diameter of the entrance of groove 48 is at least slightly smaller than the outer diameter 126 of an uncompressed snap ring 28. Opening 114 of snap ring 28 has an inner diameter, which allows snap ring 28 to fit around upper portion 80 of washer 26. One of the surfaces 118 and 120 engage the upper surface 83 of lower portion 82 in order to secure washer 26. Snap ring 28 can have a square cross-section, as shown in FIG. 1, or a circular or other appropriate shape cross-section, and in one particular embodiment is made of a shape memory alloy such as nitinol.

Figure 17A:
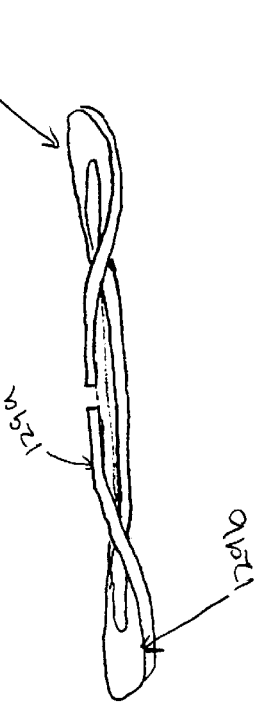
FIG. 17a shows a side view of an alternative embodiment of a snap ring for use in the present invention.

Another embodiment of snap ring 28' is illustrated in FIG. 17a. Snap ring 28' is non-planar, and in one embodiment has a series of undulations forming relative crests 129a and relative troughs 129b therein. Alternatively, non-planar snap ring 28' could have other curved configurations, or could have extending finger-spring elements along it. When assembly 20 (or assembly 262 described below) is assembled, non-planar snap ring 28' allows less play between saddle member 22, anchoring member 24 and washer 26 (or similar parts of assembly 262, described below) because non-planar snap-ring 28' fills a greater portion of groove 48 of saddle member 22.

An embodiment of an orthopedic fixation plate 130 according to the present invention is illustrated in FIGS. 19–23. In one form, orthopedic plate 130 is secured to the occipital bone of a skull. However, it should be appreciated that plate 130 can be secured to other bones. Orthopedic plate 130 includes a cross-shaped member 132 having a first longitudinal arm (end) 134 to a second longitudinal arm (end) 136 along a longitudinal axis. Cross-shaped member 132 further has a first transverse arm (end) 138 and a second transverse arm (end) 140 connected together along an axis transverse with respect to the longitudinal axis. Orthopedic plate 130 further includes a pair of saddle members 22a integrally formed on or joined to longitudinal arms 134 and 136. It should be appreciated that saddle members 22 can also be pivotally coupled to cross-shaped member 132 so as to provide greater positioning freedom. As illustrated in FIG. 22, saddle members 22a each include a pair of upright members 32a and a channel 34a defined between upright members 32a. Upright members 32a include threaded portions 52a configured to be threadedly coupled to a set screw 30 in a manner as described above.

Orthopedic plate 130, in one embodiment, includes a set of apertures 142. Bone anchors 24b (FIG. 6a) are secured in apertures 142 in order to secure plate 130 to the occipital bone of the skull. As shown in FIG. 6a, anchor 24b includes a head portion 58b having a convex underside 59a, which may be spherical, and a beveled top 59b around a tool-engaging recess 59c. Apertures 142 shown in FIGS. 19–23 for the particular embodiment are provided on both the longitudinal arms 134, 136 and the transverse arms 138, 140 in a cross configuration in order to provide greater stability. As shown in FIG. 23, aperture 142 includes a lower conical portion 144 and an upper conical portion 146. Lower conical portion 144 widens towards a lower surface 148 of orthopedic plate 130, and upper conical portion 146 widens towards an upper surface 150 of orthopedic plate 130. Upper and lower conical portions 144,146 allow a bone screw to be easily positioned at varying angular positions relative to orthopedic plate 130. In one embodiment, opposing walls of lower conical portion 146 are oriented at about sixty degrees (60°) with respect to one another, and opposing walls of upper conical portion 146 are oriented at about forty-five degrees (45°) with respect to one another. Cross member 130 further includes a beveled outer peripheral surface 152 between lower surface 148 and upper surface 150.

In one particular embodiment, cross member 132 is curved along the longitudinal axis between longitudinal arms 134 and 136, and is also slightly curved along the transverse axis. This curvature of cross member 132 allows orthopedic plate 130 to better match the contour of the occipital bone of the skull. It should be understood that cross member 132 can also be curved along only one of the axes or substantially flat along both axes or can be otherwise contoured prior to or during surgery in order to match specific patient anatomy.

Figure 24:
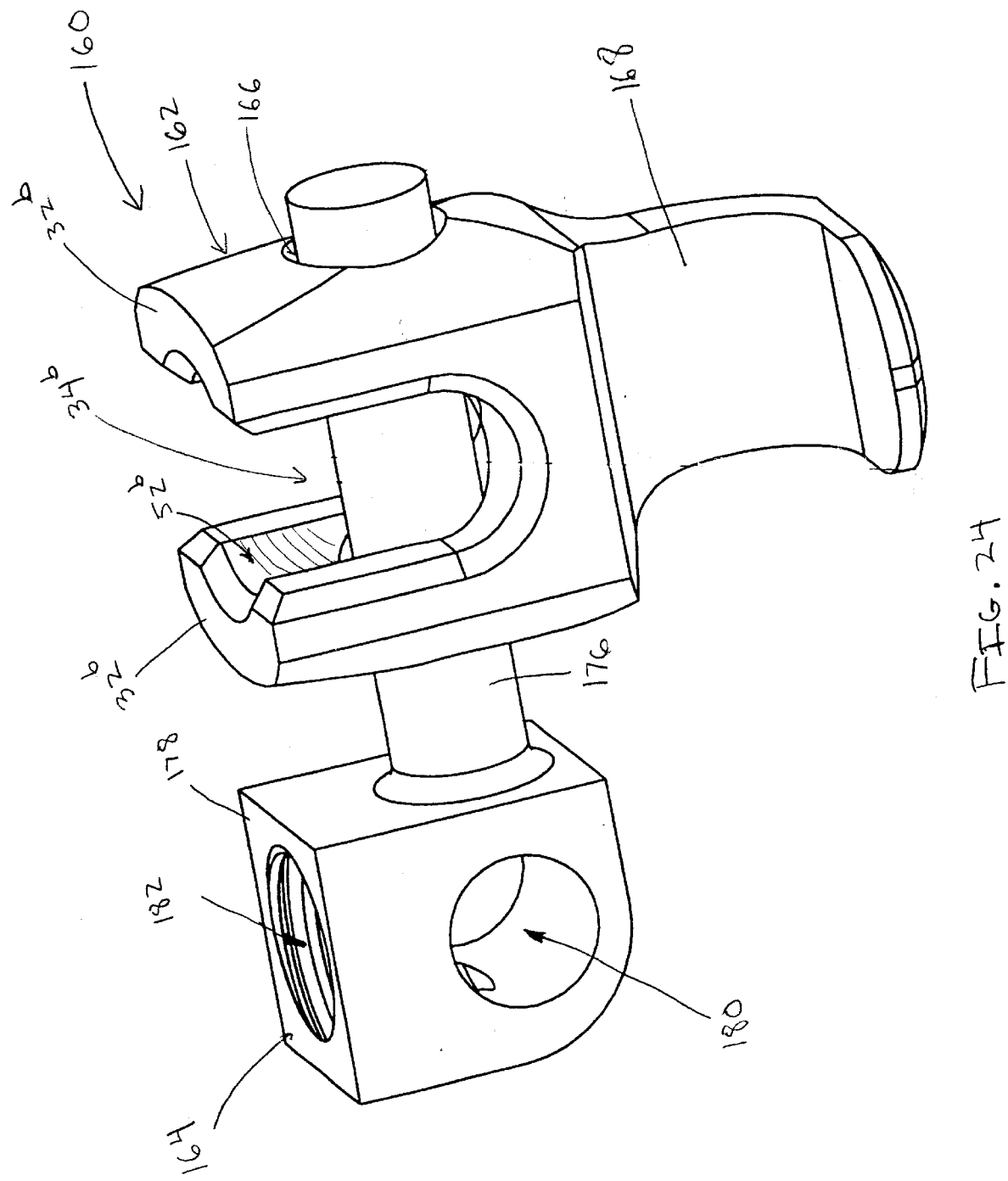
FIG. 24 shows a perspective view of a bone anchor assembly according to another embodiment of the present invention.
Figure 25:
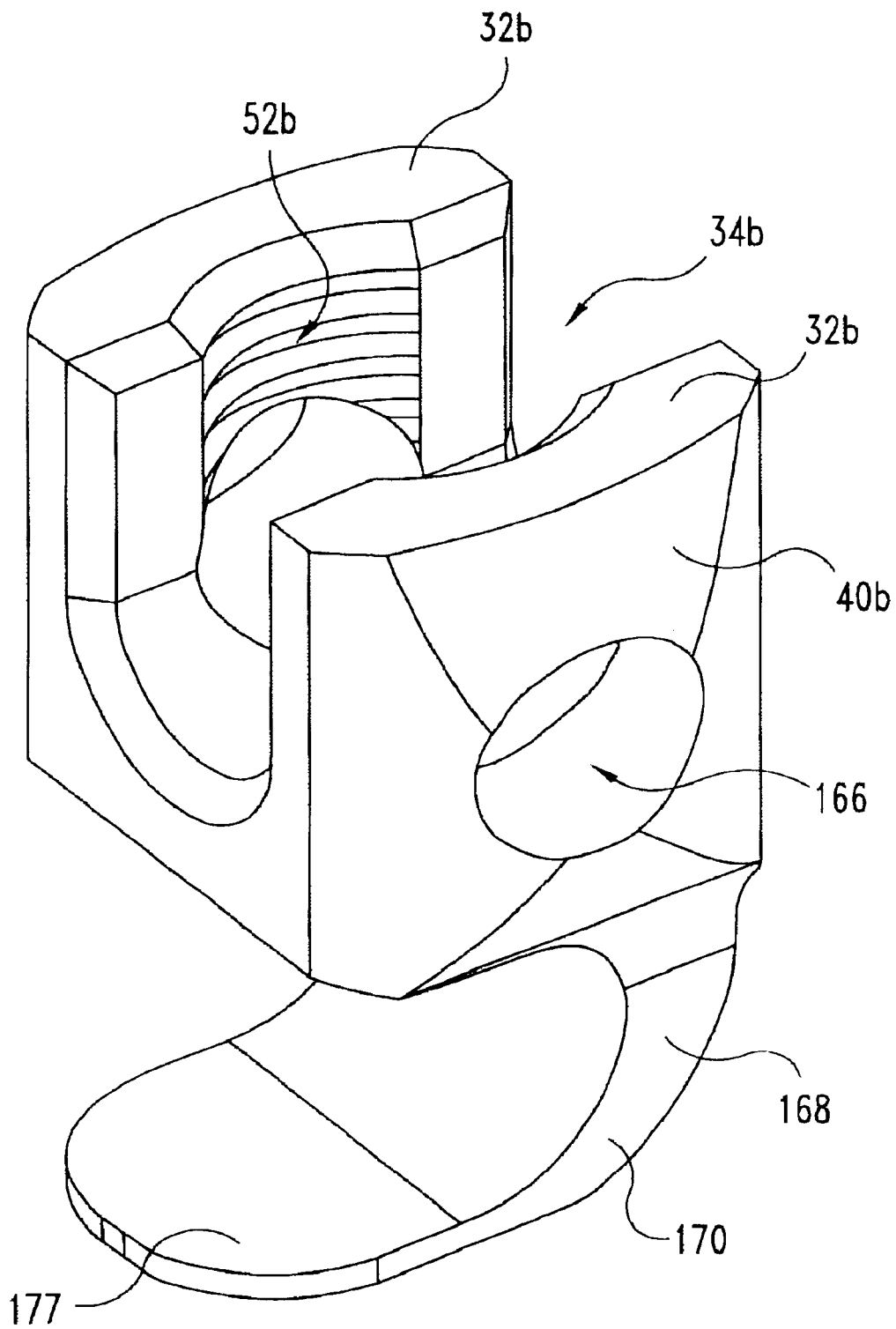
FIG. 25 shows a perspective view of an embodiment of a hook member of the assembly of FIG. 24.
Figure 26:
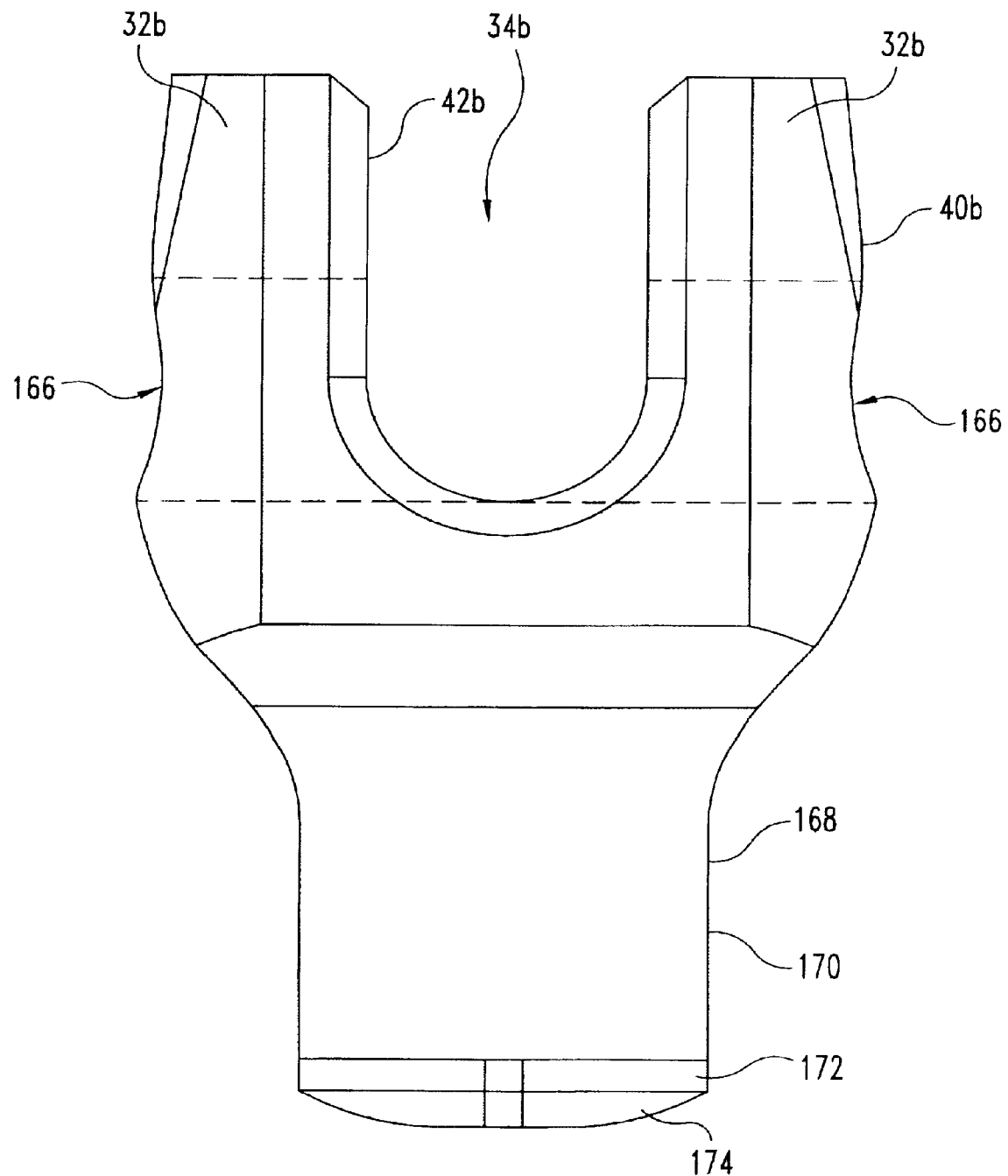
FIG. 26 shows a front view of the hook member of FIG. 25.

In FIG. 24, there is shown another embodiment of a multi-axial bone anchor assembly 160 according to the present invention. Anchor assembly includes a saddle member 162 and an offset connector 164 coupled to saddle member 162. As shown in FIGS. 25–26, saddle member 162 essentially includes the same features as described above in reference to saddle member 22. Saddle member 162 includes two upright portions 32b defining channel 34b. Channel 34b is configured to accommodate an elongated member 36b. Upright portions 32b each has outer surface 40b that is angled with respect to inner surface 42b. Upright portions 32b further include an internally threaded portion 52b. Internally threaded portions 52b are configured to be threadedly coupled with set screw 30.

Additionally, saddle member 162 includes a transverse hole 166 defined in both upright portions 32b. Transverse hole 166 is oriented transverse with respect to channel 34b, and transverse hole 166 is adapted to receive a rod (such as rod 36 in FIG. 1) or offset connector 164. This configuration between channel 34b and transverse hole 166 provides a physician with greater flexibility during surgery, since offset connector 164 can be oriented at different angles with respect to saddle member 162. Offset connector 164 further can be laterally positioned at any of an infinite number of distances from saddle member 162, because transverse hole 166 passes through both upright portions 32. Further, saddle member 162 is dually useful, because a rod (such as rod 36 in FIG. 1) or offset connector 164 can be coupled to either channel 34b or transverse hole 166.

Saddle member 162, in one embodiment, further includes a hook member 168 for engaging bones in a generally known manner. Hook member 168 has a curved portion 170 extending from upright portions 32 and a substantially straight portion 172 extending from curved portion 170. Straight portion 174 has a beveled bottom surface 174, which reduces trauma when hook member 168 is attached.

It should be appreciated that hook member 168 could be replaced with another anchoring member, such as anchoring members 24 or 24*a* (FIGS. 6, 53) in order to attach saddle member 162 to a bone.

Referring now generally to FIGS. 27–32, offset connector 164 includes a coupling member 176 integrally formed or otherwise joined to a body 178. In one form, coupling member 176 is a cylindrical rod. Body 178 has a rod receiving bore 180 that is adapted to receive rod 36 and a threaded bore 182 that intersects rod receiving bore 180. A set screw 30 is screwed into threaded bore 182 in order to secure rod 36 to offset connector 164. Body 178 further can include a beveled outer edge 184 (FIG. 27) in order to minimize trauma to a patient. In another embodiment shown in FIGS. 28–32, rod receiving bore 180 has a slot 186 defined therein. Edges 187 are formed between slot 186 and rod receiving bore 180. Edges 187 along with set screw 30 provide three lines of contact with a rod 36 coupled to offset connector 164 so as to strengthen the connection. In still yet another embodiment shown in FIG. 28*a*, offset connector 164*a* has a pair of upright portions 32*c* defining a channel 34*c* adapted to receive a rod. Upright portions 32*c* have internally threaded portions 52*c* for engaging a set screw 30.

Figure 27:
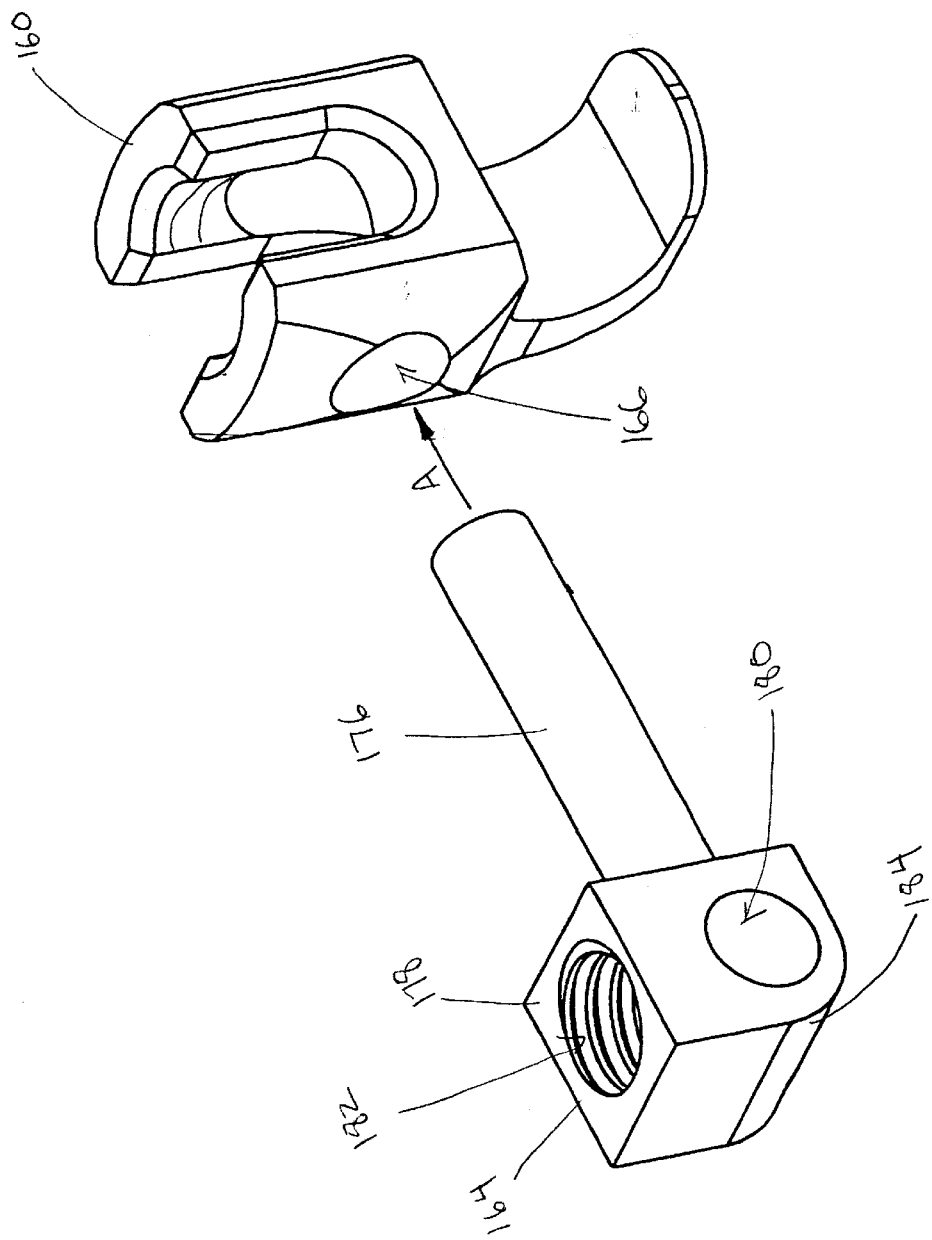
FIG. 27 shows a perspective view of the bone anchor assembly of FIG. 24 prior to assembly.
Figure 28A:
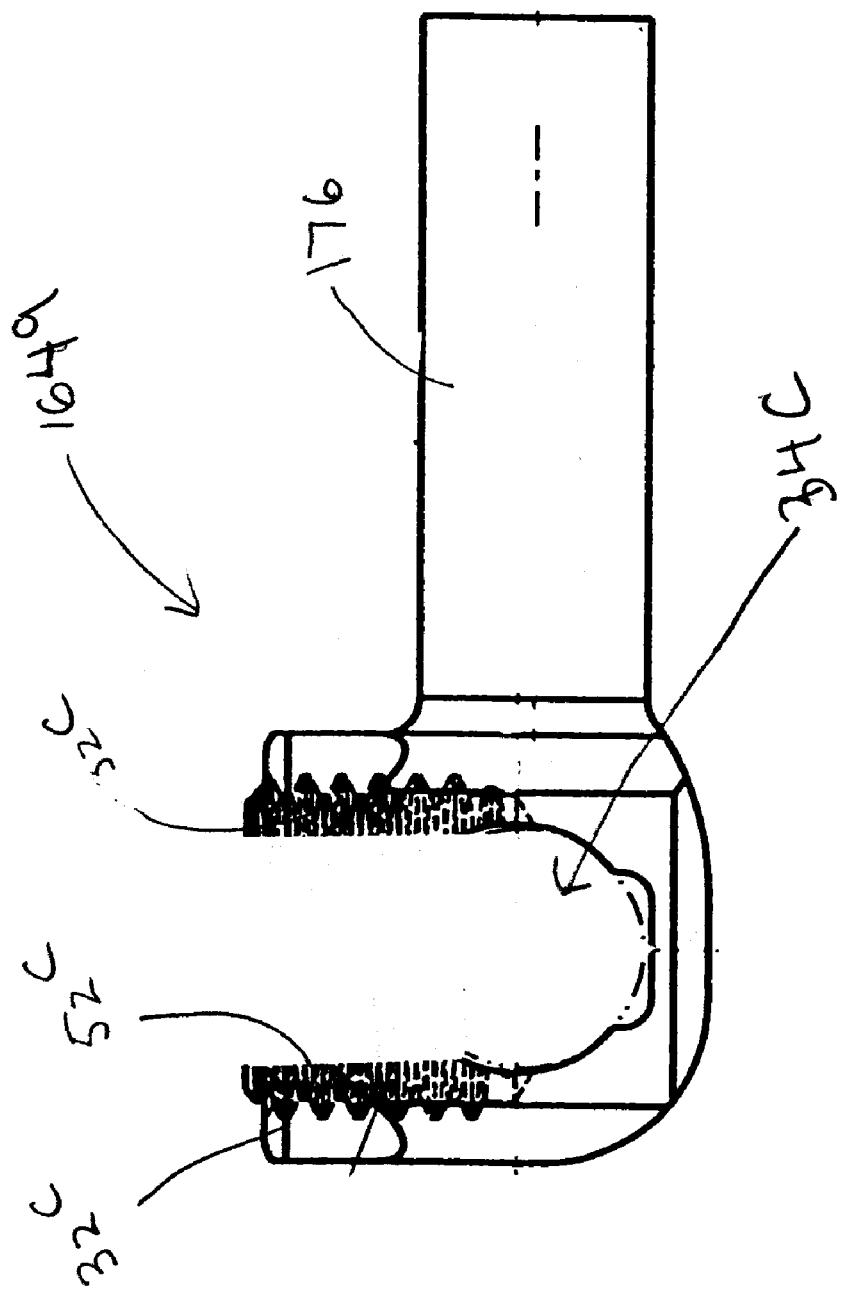
FIG. 28a shows a partial cross-sectional view of an offset member according to a further embodiment of the present invention.
Figure 33:
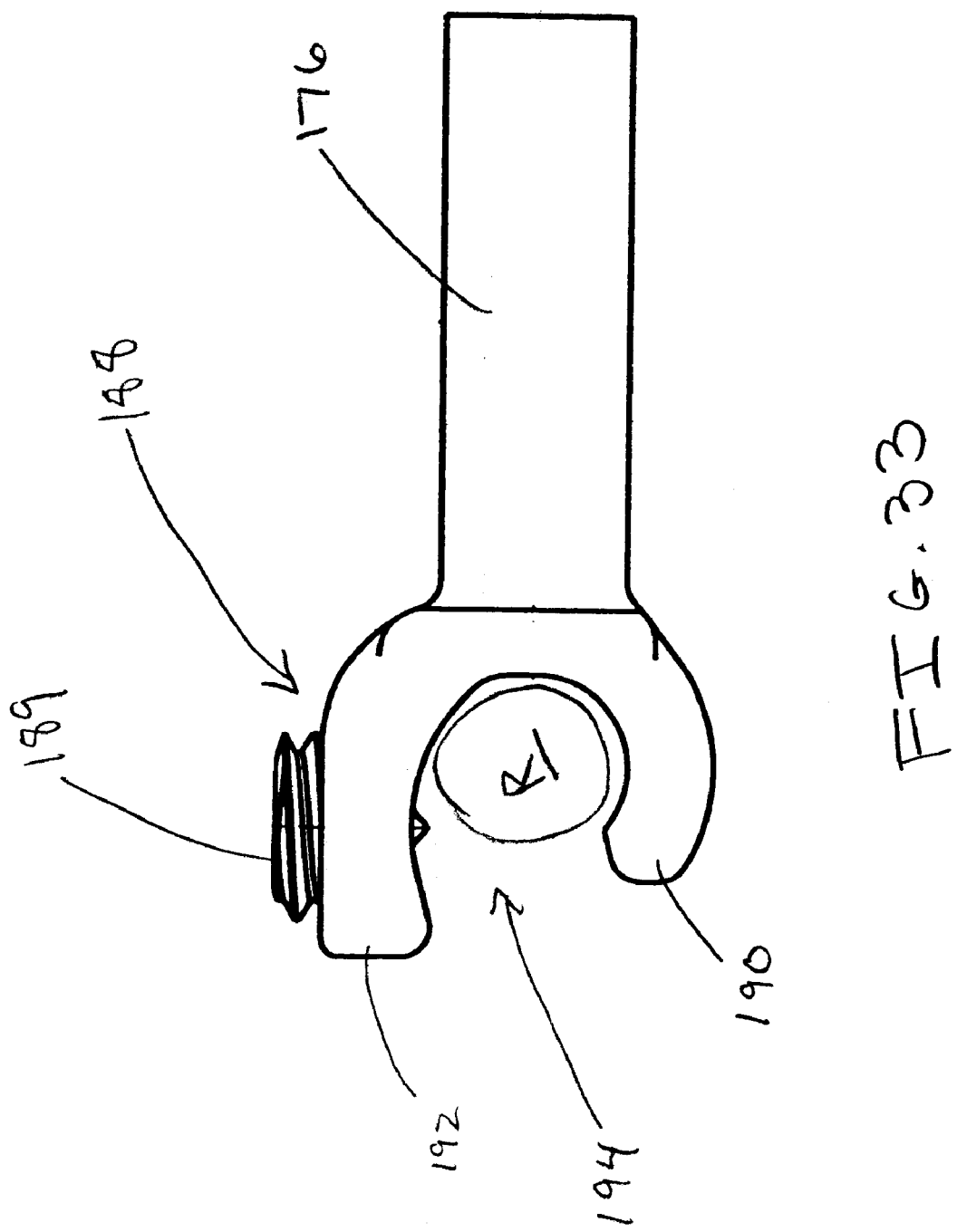
FIG. 33 shows a side view of an offset member and a set screw according to a further embodiment of the present invention.

Referring now to FIG. 27, offset connector 164 is coupled to saddle member 162 by inserting coupling member 176 in direction A into transverse hole 166. Set screw 30 is used to secure coupling member 176 to saddle 160. Offset connector 164 can be laterally positioned with respect to saddle member 162 by moving coupling member 176 within transverse hole 166.

Figure 38:
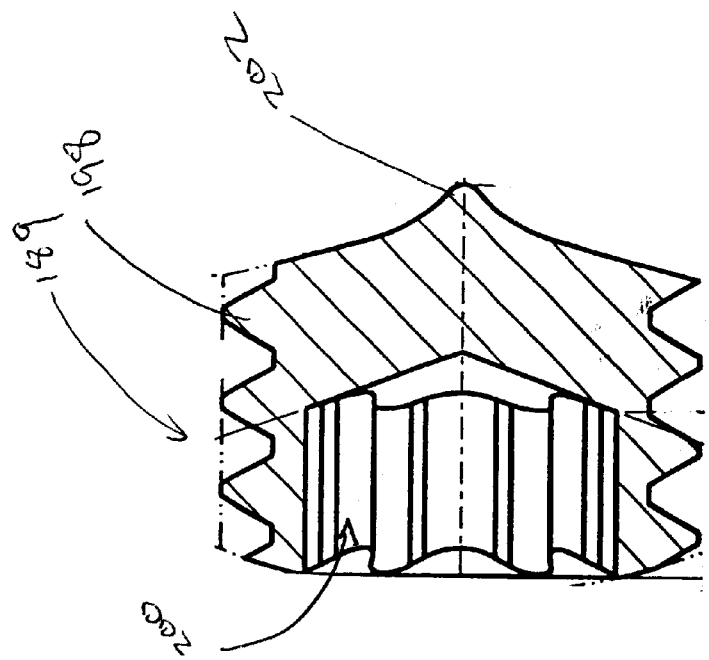
FIG. 38 shows a cross-sectional view of the set screw taken along line XXXVIII—XXXVIII in FIG. 37.
Figure 37:
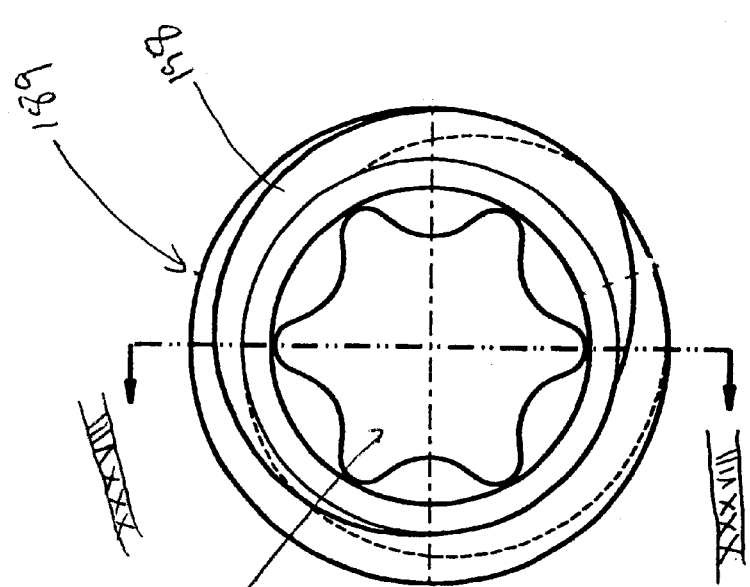
FIG. 37 shows an end view of the set screw of FIG. 33.
Figure 39:
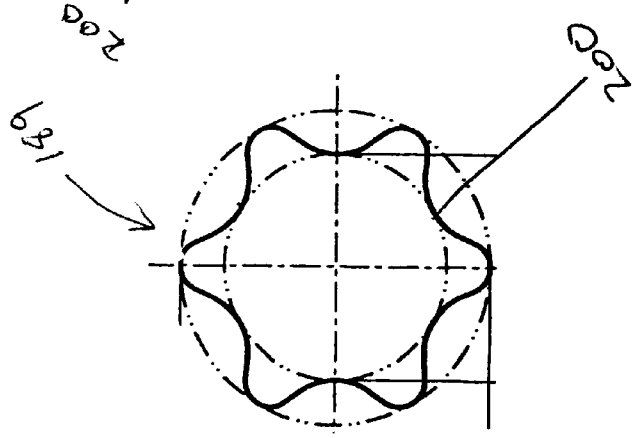
FIG. 39 shows a cross-sectional view of the set screw of FIG. 37.

An offset connector 188 along with a set screw 189 according to still yet another embodiment of the present invention are shown in FIGS. 33–39. As shown in FIGS. 33–36, offset connector 188 includes a coupling member 176, and a pair of laterally oriented body members 190 and 192. A channel 194 is defined between body members 190 and 192, and channel 194 is adapted to receive rod 36. One of the body members 192 is slightly longer than the other and has a threaded bore 196 defined therein. Set screw 189 is threaded into bore 196 so as to secure rod R to offset connector 188. As illustrated in FIGS. 37–39, set screw 189 is generally cylindrical and has threads 198. Set screw 189 further has a tool engaging bore defined in one end and a pointed tip 202 at the other end. Pointed tip 202 engages rod 36 when rod 36 is coupled to offset connector 188.

Figure 43:
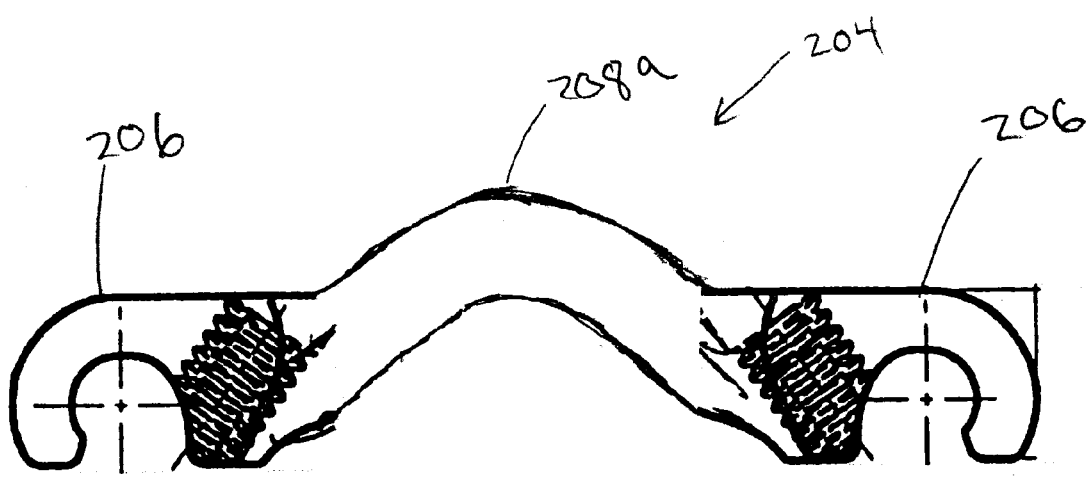
FIG. 43 shows a cross-link connector with an arched cylindrical member.
Figure 42:
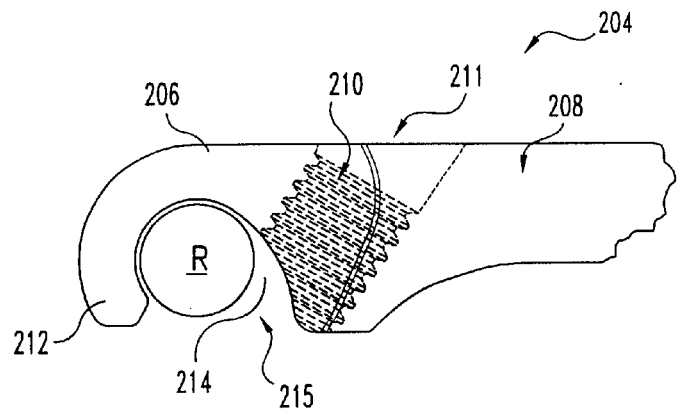
FIG. 42 shows an enlarged view of a portion of the cross-link connector of FIG. 40.
Figure 41:
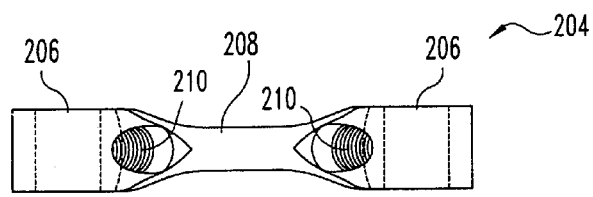
FIG. 41 shows a top view of the cross-link connector of FIG. 40.
Figure 40:
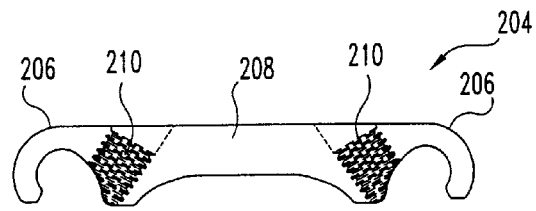
FIG. 40 shows a side view of a cross-link connector according to another embodiment of the present invention.
Figure 43:
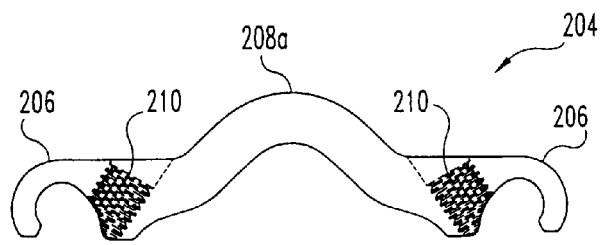
Figure 45:
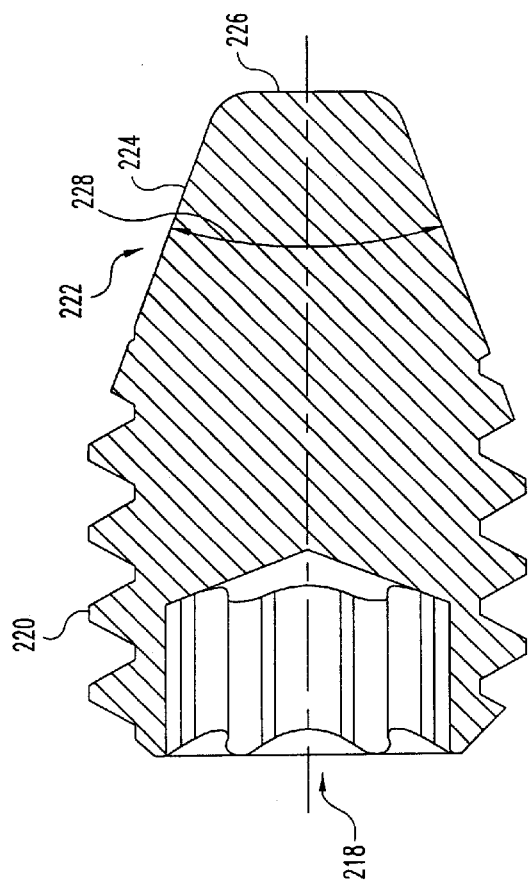
Figure 44:
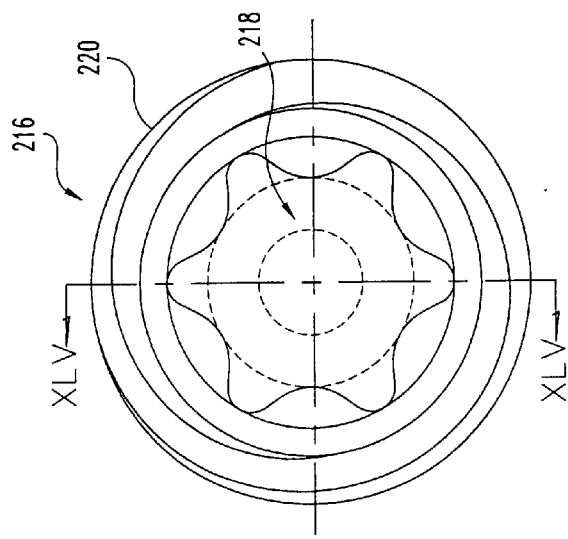
Figure 48:
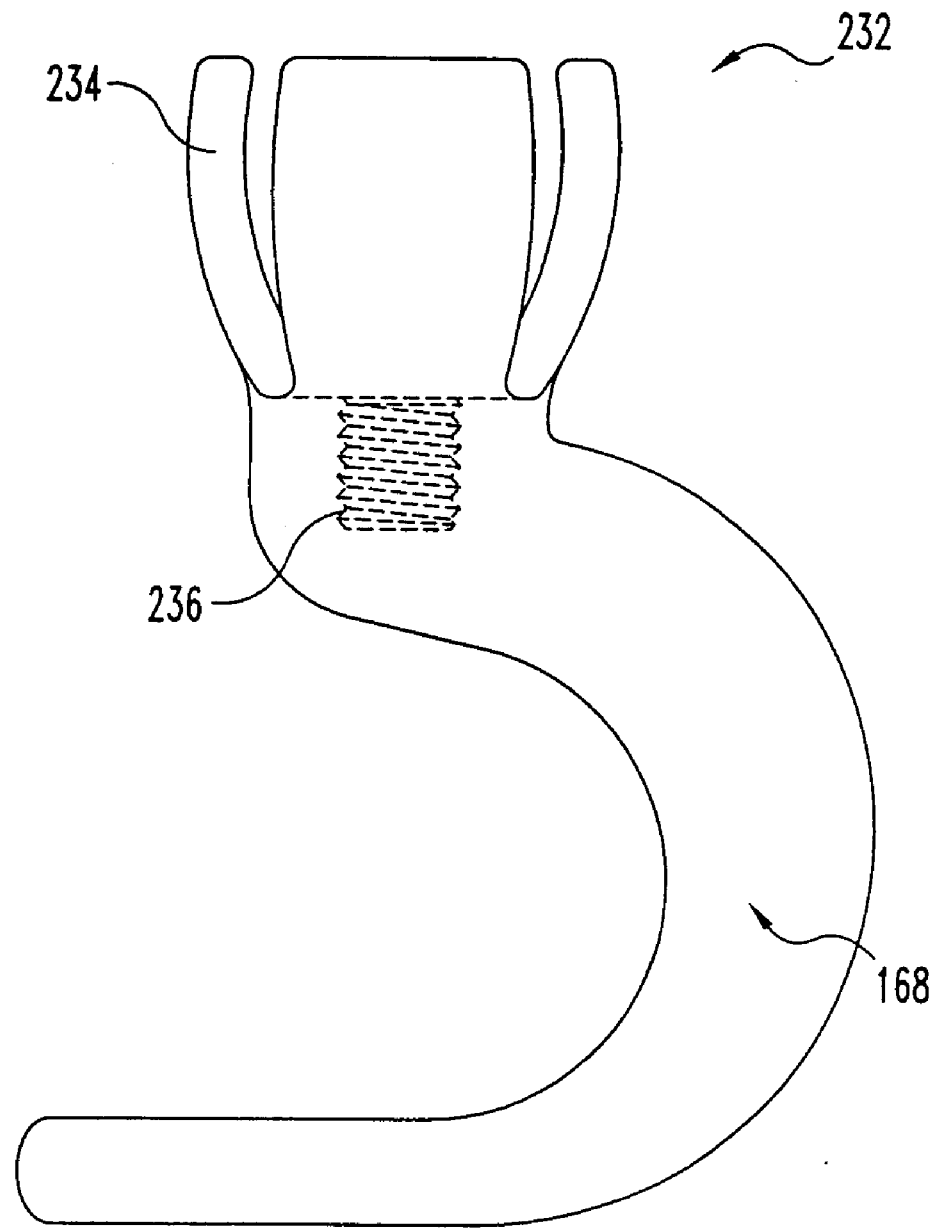
Figure 49:
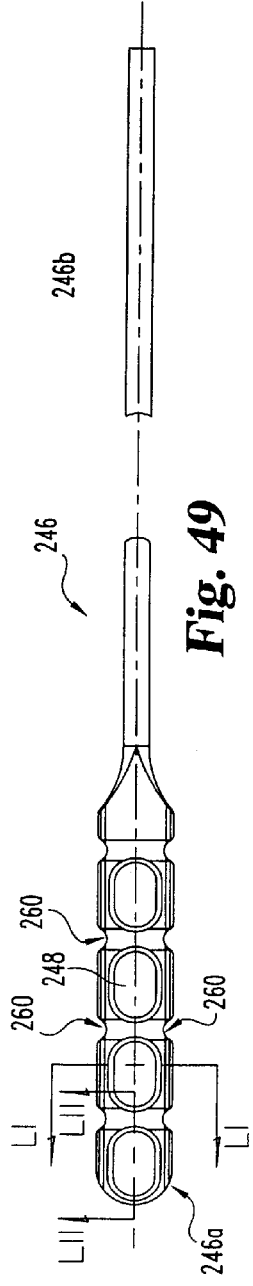
FIG. 49 shows a top view of an occipital-cervical rod.
Figure 50:
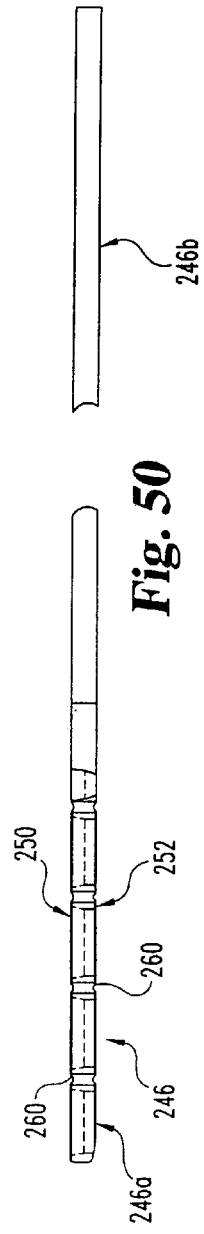
FIG. 50 shows a side view of an occipital-cervical rod.
Figure 52:
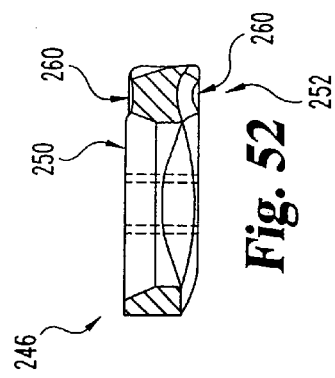
FIG. 52 shows a cross-sectional view of the occipital-cervical rod taken along line LII—LII in FIG. 49.
Figure 51:
FIG. 51 shows a cross-sectional view of the occipital-cervical rod taken along line LI—LI in FIG. 49.
Figure 53:
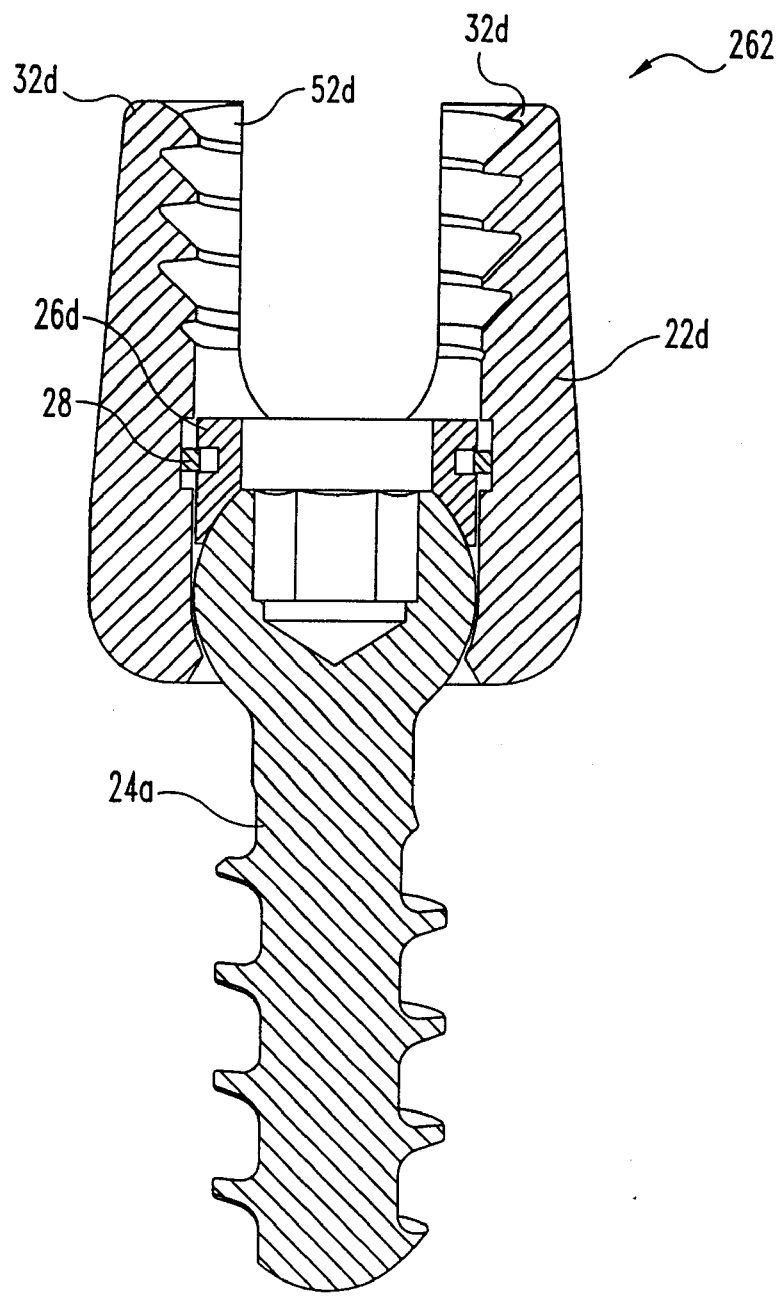

A cross-link connector 204 according to one embodiment, which is illustrated in FIGS. 40–42, is adapted to be bent about multiple axes. Cross-link connector 204 has a pair of coupling ends 206 integrally connected together with a cylindrical member 208. The cylindrical shape of cylindrical member 208 allows cross-link connector 204 to be bent in any of an infinite number of directions. In one particular embodiment shown in FIG. 43, cylindrical member 208*a* is pre-formed with an arch so as to avoid any obstructions between the two ends 206. Each coupling end 206 includes a threaded bore 210 with an opening 211 in which a set screw 30 is threaded and a curved member 212 that defines a cavity 214 adapted to receive rod R. Opening 215 of cavity 214 is defined in a side of cross-link connector 204 opposite opening 211 of threaded bore 210. This configuration allows cross-link connector 204 to be secured to adjacent rods after the adjacent rods are situated within the patient. In one embodiment, threaded bore 210 is positioned at about fifty-five degrees (55°) relative to a longitudinal axis that extends between the ends 206. Cross-link connectors are used to link adjacent rods within a patient. An obstruction (such as another rod or bone) may prevent a typical cross-link connector from linking adjacent rods together. The cross-link connector 204 of the present invention solves this problem by being adapted to bend along multiple axes.

Figure 45:
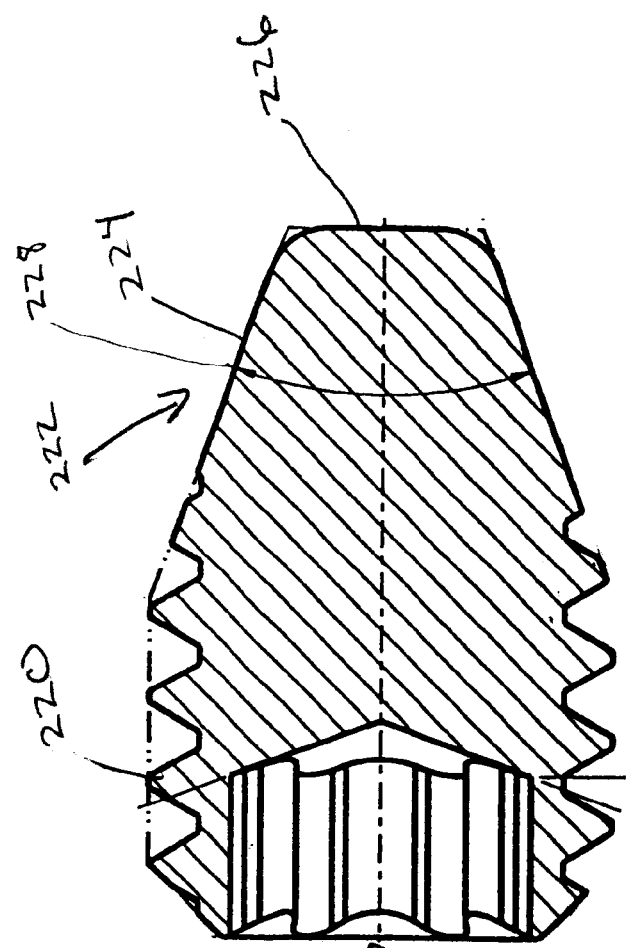
FIG. 45 shows a cross-sectional view of the set screw taken along line XLV—XLV in FIG.44.
Figure 44:
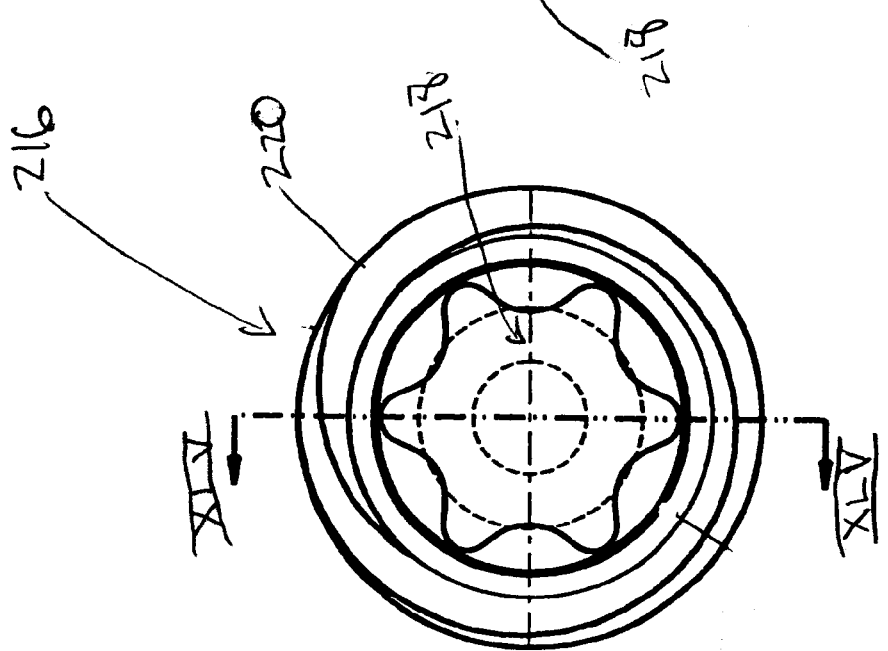
FIG. 44 shows an end view of a set screw according to another embodiment of the present invention.

One embodiment of a set screw 216 that is adapted to be threaded into threaded bore 210 is illustrated in FIGS. 44–45. Set screw 216 has one end with a tool engaging bore 218, a rod engaging end 222 and a threaded portion 220 provided between both ends. Rod engaging end 222 has a frusto-conical portion 224 adjacent threaded portion 220 and a flat portion 226, which frusto-conical portion 224 contacts rod 36. In one form, frusto-conical portion 224 has an angle 228 of about forty degrees (40°).

Figure 46:
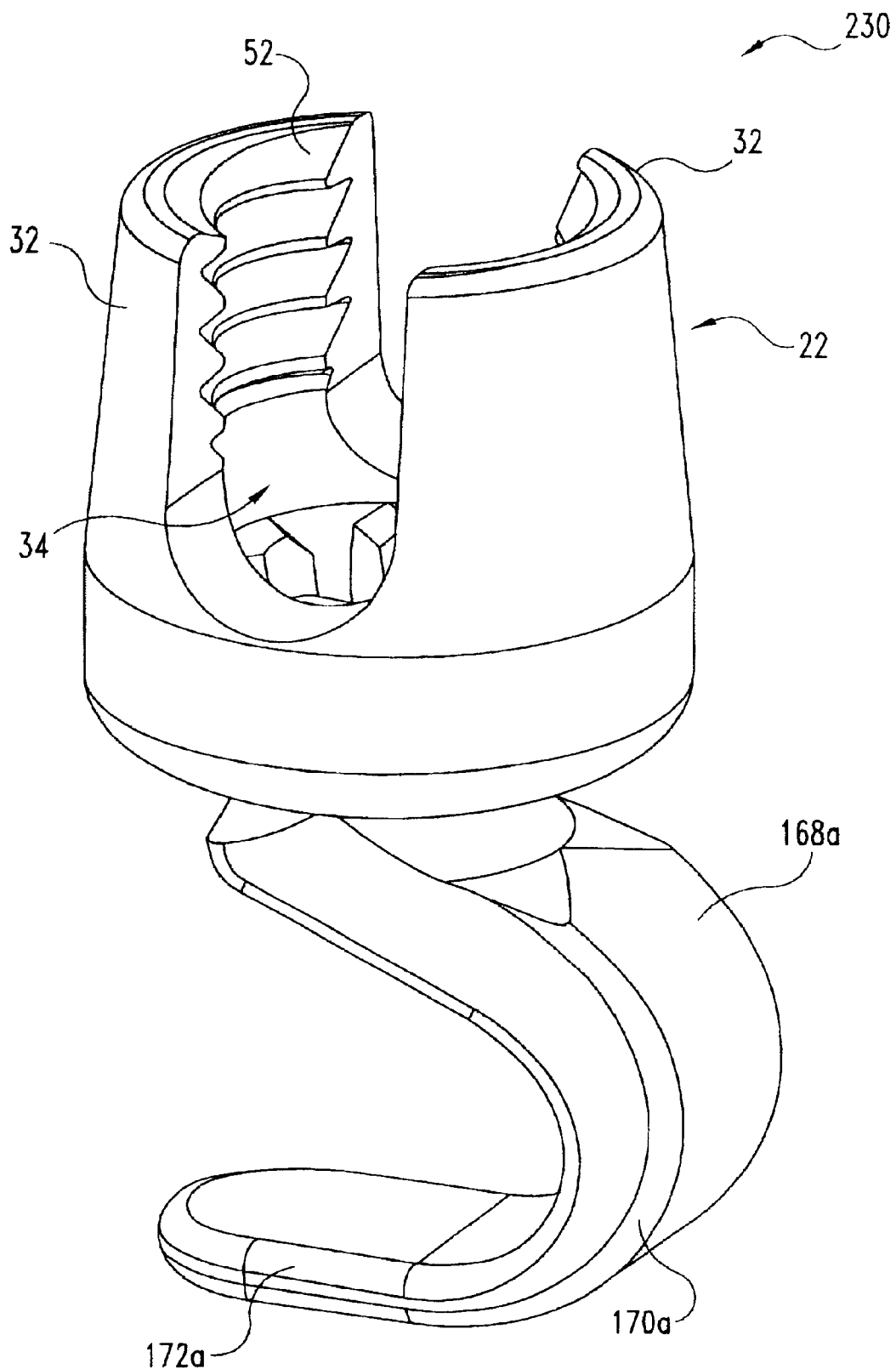
FIG. 46 shows a perspective view of a bone anchor assembly according to a further embodiment of the present invention.
Figure 47:
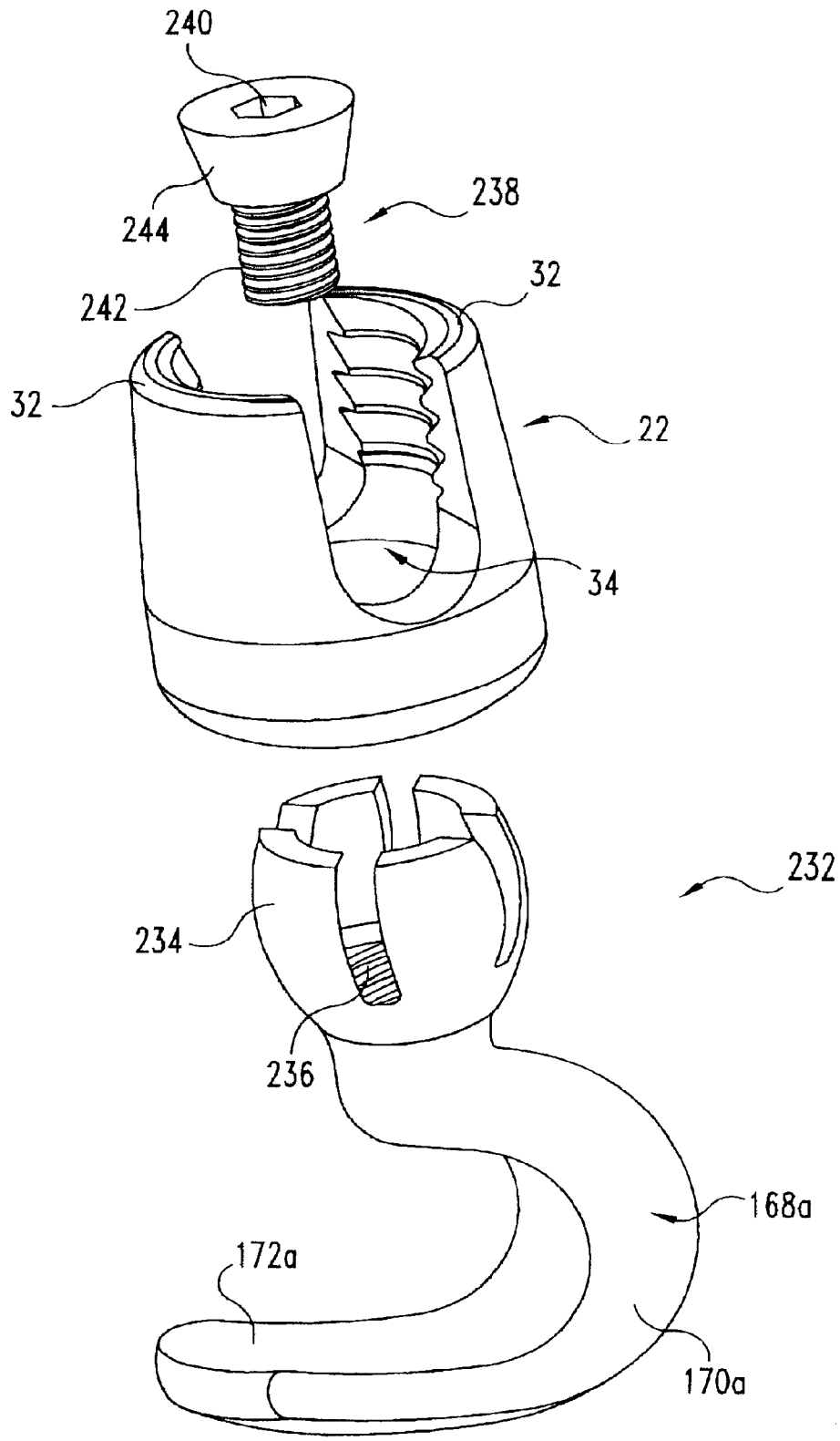
FIG. 47 shows an exploded view of the bone anchor assembly of FIG. 46.
Figure 48:
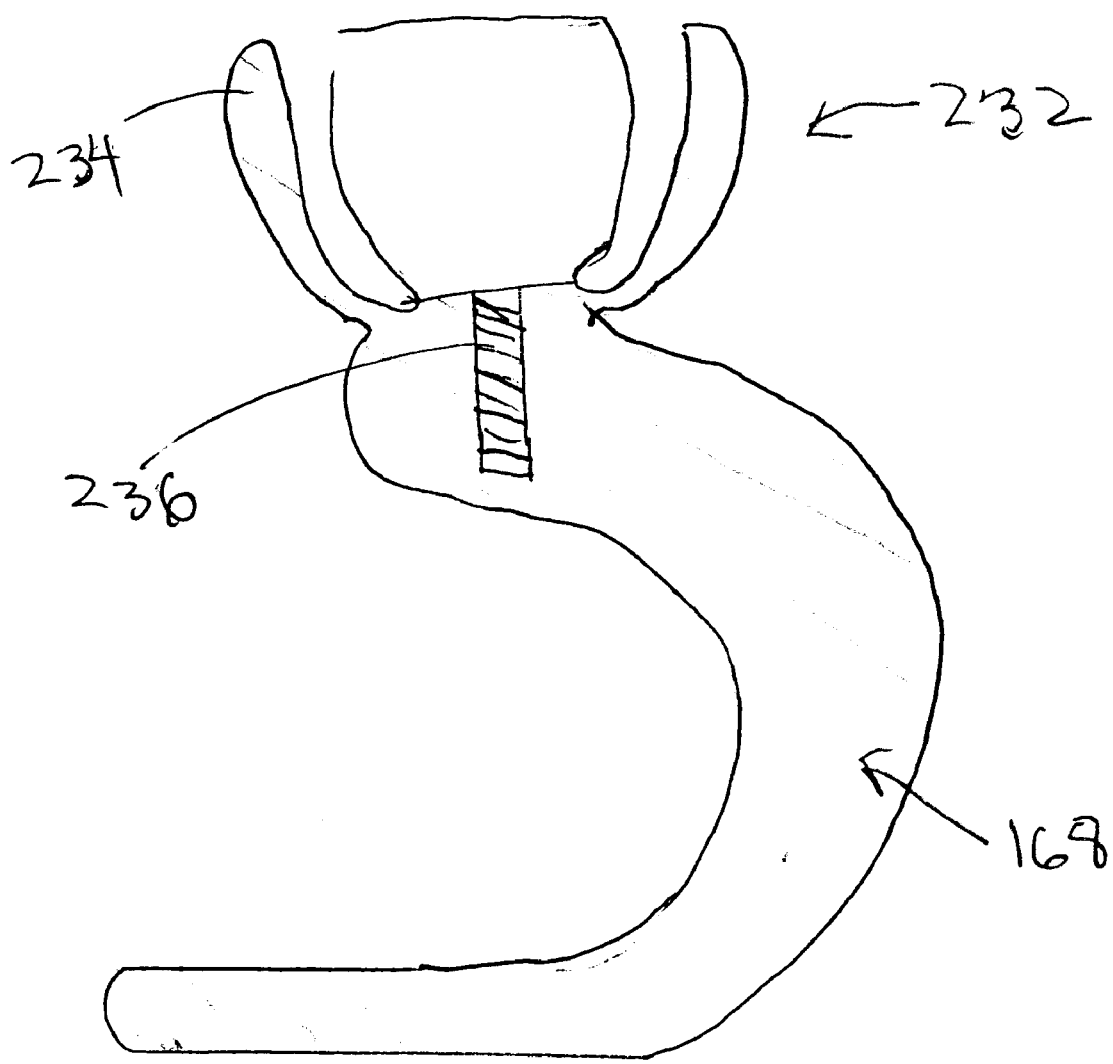
FIG. 48 shows a cross-sectional view of a hook member.

In FIG. 46, there is shown a multi-axial bone anchor assembly 230 according to another embodiment of the present invention. Assembly 230 has a generally U-shaped saddle member 22, which was described above with reference to FIGS. 2–5, coupled to a hook anchor member 168*a*. In this embodiment, saddle member 22 may be formed without groove 48. As previously discussed, saddle member 22 has a pair of upright portions 32 that define channel 34. Set screw 30 is threadedly secured to threaded portion 52 of saddle member 22 in order to secure rod 36 to saddle member 22. As shown in FIGS. 47–48, hook member 168*a* has a curved portion 170*a* and a substantially straight portion 172*a*. In this embodiment, hook member 168*a* further includes a coupling (head) portion 232 that is coupled to saddle member 22. Coupling portion 232 includes coupling members 234 and a threaded hole 236 adapted to receive expansion member 238. In one form, coupling portion 232 includes four members 234 having a part-spherical outer surface and expansion member 238 is a set screw. In one form, expansion member 238 at one end has a tool engaging portion 240 and a threaded portion 242 at the other end for securing expansion member 238 into hole 236. Expansion member 238 further includes an expansion portion 244 located between tool engaging portion 240 and threaded portion 242. Expansion portion 244 contacts and expands semispherical members 234 to anchor saddle member 22 to hook member 168 and prevents further rotation. In one form, expansion portion 244 has a conical shape.

In use, coupling portion 232 is inserted into hole 38 through the bottom of saddle member 22. When saddle member 22 is coupled to hook member 168*a*, the spherical shape formed between semispherical members 234 allows saddle member 22 to rotate about multiple axes. Expansion member 238, once secured in hole 236 causes coupling members 234 to splay into contact with saddle member 22, thereby fixing the relative position between saddle member 22 and hook member 168.

An embodiment of an occipital-cervical rod 246, which can be attached to the above-described assemblies, is illustrated in FIGS. 49–52. Occipital-cervical rod 246 includes a plate portion 246*a*, through which a plurality of apertures 248 are formed, and a rod portion 246*b*. Apertures 248 may be oblong in shape. Defined along plate portion 246*a* are an upper surface 250, a curved lower surface 252, and a pair of beveled side surfaces 254 between upper surface 250 and lower surface 252. Each aperture 248 includes an upper portion 256 that widens towards upper surface 250 and a lower portion 258 that widens towards lower surface 252. Grooves 260 are defined around plate portion 246*a* of occipital-cervical rod 246 and between adjacent apertures 248. Bone screws 24*b* (FIG. 6*a*) are inserted into apertures 248 in order to secure plate portion 246*a* to the occipital bone of a patient. Rod portion 246*b* extends along the spinal column and can be attached to the spinal column using the above-described or other connectors. Alternatively, plate portion 246a can be attached to one or more vertebrae using bone screws 24b (FIG. 6a), and rod portion 246b can extend upward and be attached to the occipital bone using screws, hooks, cable, or other attachment members.

Figure 53:
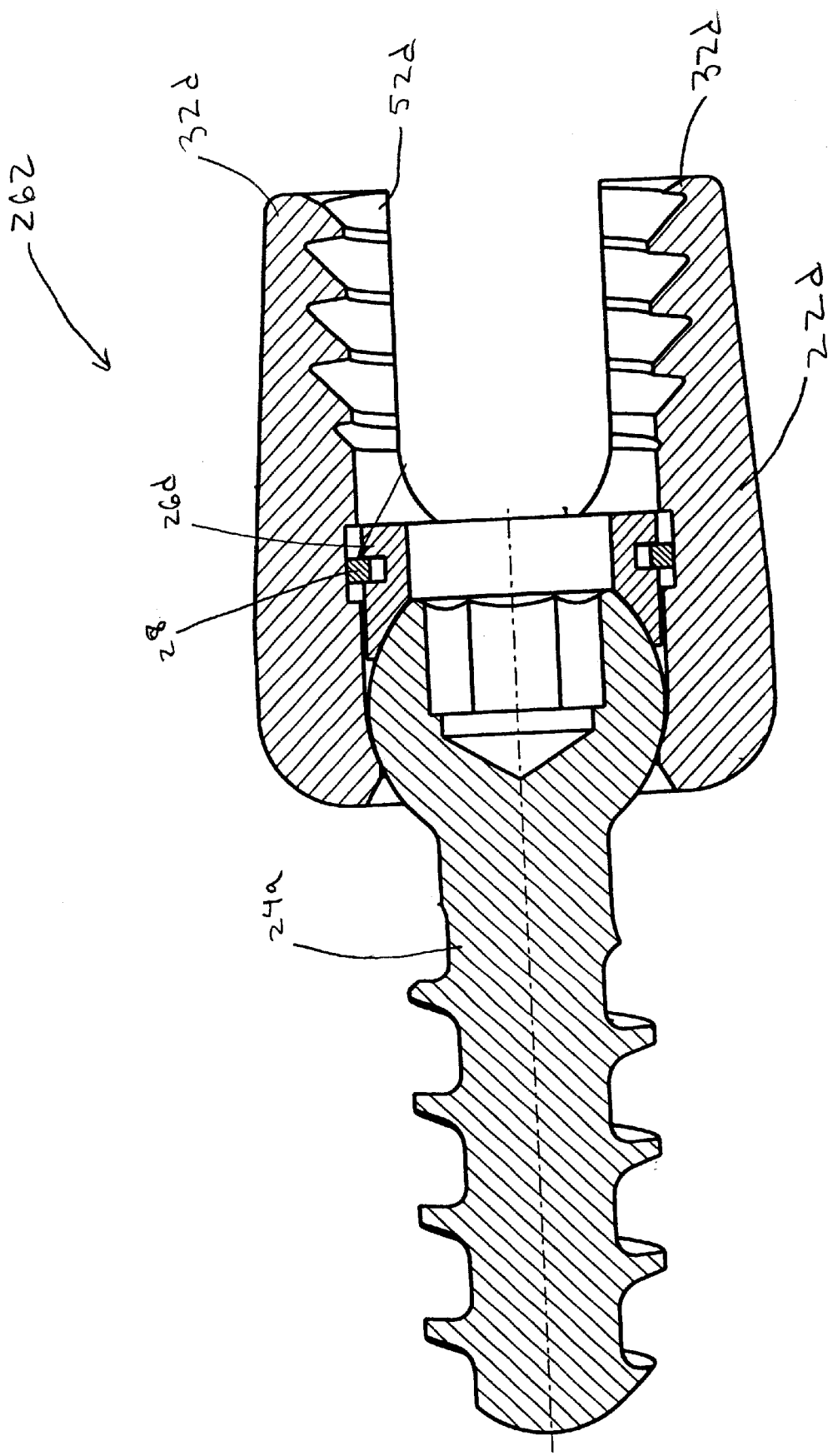
FIG. 53 shows a partial cross-sectional view of a bone anchor assembly according to another embodiment of the present invention.

In FIG. 53, there is shown another embodiment of a multi-axial bone anchor assembly 262 according to the present invention. Bone anchor assembly 262 includes a saddle member 22d, a bone anchoring member 24a, and a washer 26d. Bone anchoring member 24a does not have a lip 74. In some embodiments, assembly 262 will further include a C-shaped snap ring 28 and a set screw 30, which are fitted with saddle member 22d in a manner described below.

Figure 54:
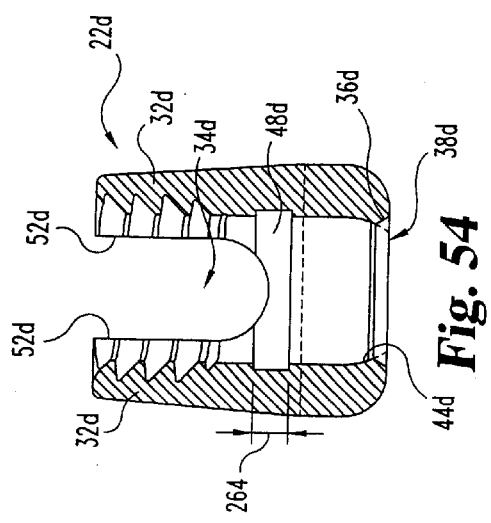
FIG. 54 shows a cross-sectional view of an embodiment of a saddle member shown in FIG. 53.
Figure 55:
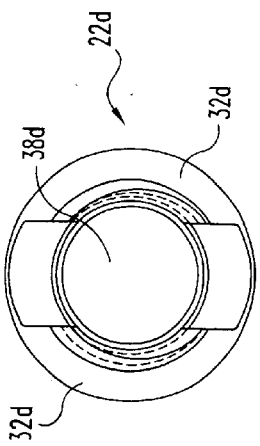
FIG. 55 shows a top view of the saddle member of FIG. 54.

As shown in FIGS. 54–55, saddle member 22d generally has a U-shape, with two upright portions 32d defining a channel 34d extending through saddle member 22d. Channel 34d is then configured to accommodate an elongated member 36 (as described above). Saddle member 22d further includes a hole 38d therethrough, hole 38d being in one particular embodiment substantially perpendicular to channel 34d and substantially parallel to upright portions 32d. Upright portions 32d are angled in a manner similar to the one as described above with reference to FIGS. 2–3. Near the bottom of saddle member 22d, hole 38d is narrowed by a wall portion 44d. Below wall portion 44d, hole 38d opens outward by virtue of a wall portion 46d. Wall portion 46d allows bone anchor member 24a to be positioned in any of an infinite number of angular positions relative to saddle member 22d by reducing interference of the lower portion of saddle member 22d with a shank portion of bone anchor member 24a.

The particular illustrated embodiment of saddle member 22d further includes an inner groove 48d. As illustrated, groove 48d extends around hole 38d, and in this particular embodiment, groove 48d is uniform between a top portion of groove 48d and the bottom portion thereof. Groove 48d is configured to accommodate snap ring 28 in a compressed condition. Groove 48d has a thickness 264 that is, in one form, thicker than snap ring 28. Further, the illustrated embodiment of saddle assembly 22d in FIGS. 54–55 does not include a trough 50 that extends longitudinally within each of upright portions 32d. Upright portions 32d further include internally threaded portions 52d, which are configured to be threadedly coupled with set screw 30.

Figure 56:
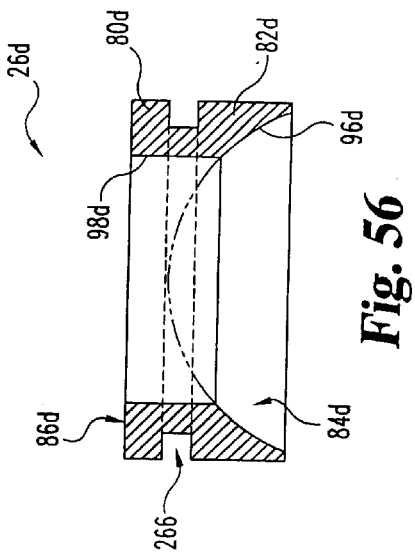
FIG. 56 shows a cross-sectional view of a washer shown in FIG. 53.

Referring now to FIG. 56, there is shown another embodiment of washer 26d according to the present invention. Washer 26d includes an upper portion 80d, a lower portion 82d, a snap ring recess 266, and a hole 84d therethrough. Upper portion 80d, lower portion 82d, and snap ring recess 266 may be constructed integrally or may be separately constructed and attached together in any known manner. Snap ring 28 fits within recess 266 in order to secure washer 26d within saddle member 22d. In one embodiment, assembly 262 is assembled by inserting anchoring member 24a through hole 38d in saddle member 22d. Washer 26d, with snap ring 28 in at least a portion of recess 266, is then inserted into hole 38d. Snap ring 28 contracts into recess 266 as washer 26d goes through saddle member 22d, and expands into groove 48d to hold washer 26d within saddle member 22d. An elongated member is then inserted in channel 34d, and a set screw (such as those described above) is threaded into internally threaded portions 52d, saddle member 22d to lock the elongated member, washer 26d and anchoring member 24a together.

Washer 26d has a hole 84d provided through both upper portion 80d and lower portion 82d. Hole 84d includes a lower concave surface 96d and a cylindrical surface 98d. Lower concave surface 96d is adapted to accommodate head portion 58a of anchor member 24a. In the particular embodiment illustrated in FIG. 56, lower portion 82d is generally in the shape of a circular disc. In this particular embodiment, lower portion 82d does not have projections 90.

While the invention has been illustrated and described in detail in the drawings and foregoing description, the same is to be considered as illustrative and not restrictive in character. It should be understood that only the preferred embodiments have been shown and described and that all changes and modifications that come within the spirit of the invention are desired to be protected.

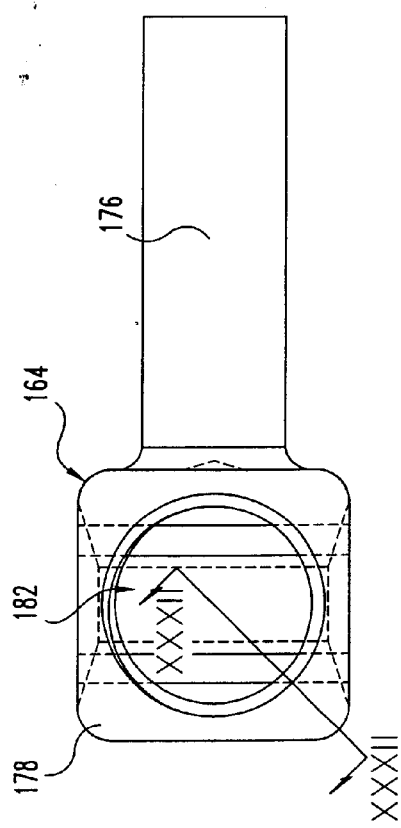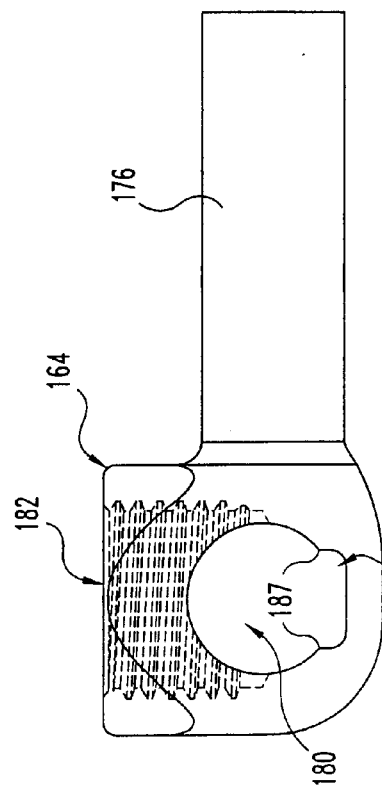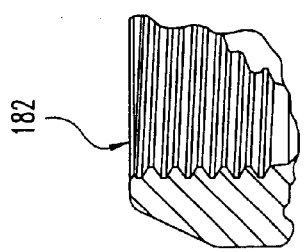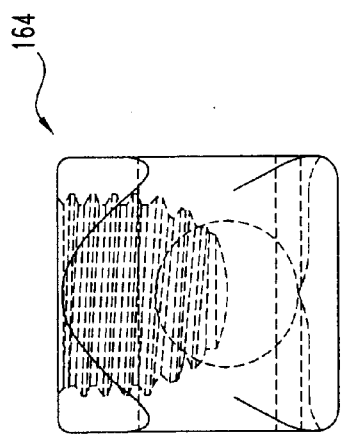

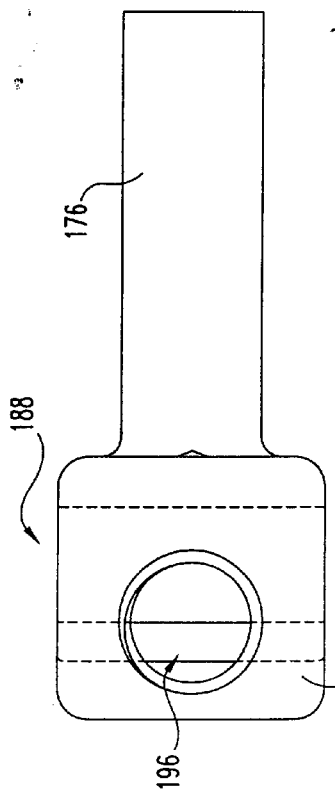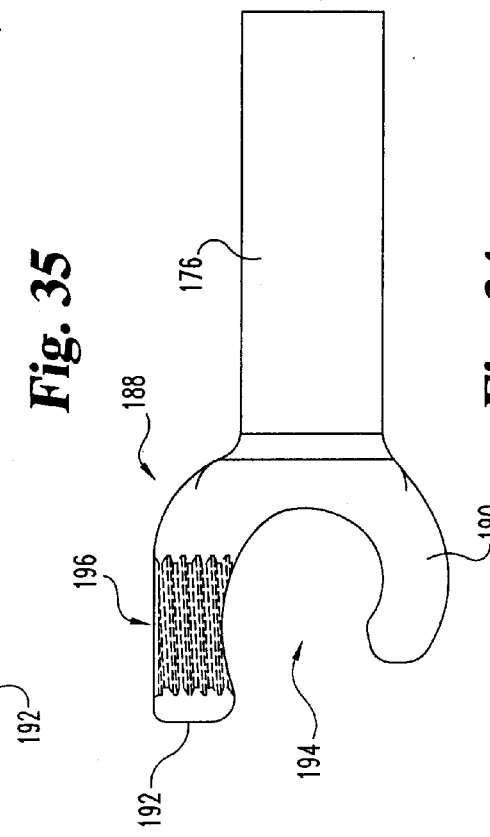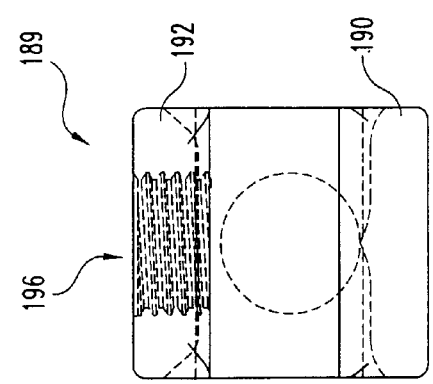

What is claimed is:

1. A multi-axial bone attachment assembly, comprising:
   a saddle member having a plurality of upright portions that define a channel through said saddle member, said saddle member further having a hole therethrough bounded by an inner wall, said hole forming a lower opening in said saddle member;
   a bone anchoring member extending through said opening, said bone anchoring member including a head portion and an anchoring portion; and
   a washer having a recessed portion for accommodating an orthopedic rod and said washer having an alignment member to minimize misalignment between the rod and said recessed portion, said washer being fitted within said hole of said saddle member and atop said bone anchoring member.

2. The assembly of claim 1, wherein said inner wall includes a groove, and said assembly further comprises a snap-ring fitted in said groove and over said washer to hold said washer in said hole of said saddle member.

3. The assembly of claim 2, wherein said upright portions include threaded portions, and said assembly further comprises a threaded member for engagement with said threaded portions.

4. The assembly of claim 3, wherein said upright portions are internally threaded, and said threaded member is an externally threaded set screw.

5. The assembly of claim 4, wherein said set screw includes an upper surface that is convexly rounded.

6. The assembly of claim 3, wherein said threaded portions have reverse angle threads.

7. The assembly of claim 1, wherein said washer includes an upper portion and a lower portion, said recessed portion being a part of said upper portion and said projection being a part of said lower portion.

8. The assembly of claim 7, wherein said inner wall includes a groove, and said assembly further comprises a snap-ring fitted in said groove and over said lower portion of said washer to hold said washer in said hole of said saddle member.

9. The assembly of claim 7, wherein said upper portion of said washer includes a plurality of recessed portions.

10. The assembly of claim 7, wherein said lower portion of said washer includes a plurality of projections.

11. The assembly of claim 1, wherein said upright portions include threaded portions, and said assembly further comprises a threaded member for engagement with said threaded portions.

12. The assembly of claim 1, wherein said anchoring member is a bone screw.

13. The assembly of claim 12, wherein said bone screw includes a head portion having a convex underside.

14. The assembly of claim 13, wherein said convex underside is spherical.

15. The assembly of claim 14, wherein said bone screw includes a portion having a thread with a load flank and a root surface, and the angle between said load flank and said root surface is acute.

16. The assembly of claim 15, wherein said angle is about 86 degrees.

17. The assembly of claim 1, wherein said anchoring member is a hook member.

18. The assembly of claim 17, wherein said anchoring portion includes a curved portion connected to said head portion and a straight portion connected to said curved portion, said head portion including a plurality of spherical portions for coupling said anchoring member to said saddle member.

19. The assembly of claim 1, wherein said upright portions each have a trough defined therein, said washer including a plurality of projections with each provided in one of said troughs.

20. The assembly of claim 1, wherein said lower opening includes a concave wall portion and a conical wall portion for allowing angular movement of said bone anchoring member.

21. A spinal implant system, comprising:
   a saddle member having a plurality of upright portions that define a channel through said saddle member, said saddle member further having a transverse hole defined through said upright portions that is transverse with respect to said channel;
   a bone anchoring member coupled to said saddle member for anchoring said saddle member to bone; and
   an offset member adapted to couple to an orthopedic rod, said offset member having a body adapted to couple to said rod and a coupling member extending from said body through said transverse hole in said upright portions.

22. The system of claim 21, wherein said upright portions include threaded portions, and said system further comprises a threaded member for engagement with said threaded portions.

23. The system of claim 22, wherein said upright portions are internally threaded, and said threaded member includes an externally threaded set screw.

24. The system of claim 22, wherein said threaded portions have reverse angle threads.

25. The system of claim 21, wherein said anchoring member includes a hook member.

26. The system of claim 21, wherein said offset member includes a rod receiving channel defined in said body for receiving said rod.

27. The system of claim 26, wherein said offset member includes a threaded bore intersecting said rod receiving channel and a threaded set screw provided in said threaded bore.

28. The system of claim 26, further comprising a slot defined in said rod receiving channel.

29. The system of claim 21, wherein said body includes a pair of body members that define a channel in said body for receiving said rod.

30. The system of claim 29, wherein said offset member has a longitudinal axis extending along said coupling member, and said body members extend parallel to said longitudinal axis.

31. The system of claim 29, wherein said offset member has a longitudinal axis extending along said coupling member, and said body members extend perpendicular to said longitudinal axis.

32. The system of claim 29, wherein one of said body members has a threaded bore defined therein and a threaded set screw provided in said threaded bore.

33. The system of claim 21, further comprising a washer having a recessed portion adapted to accommodate said orthopedic rod and a radially extending projection, said washer being fitted within said saddle member.

34. The system of claim 33, further comprising a snap ring provided in said saddle for securing said washer in said saddle member.

35. The system of claim 21, further comprising said orthopedic rod coupled to said offset member.

36. The system of claim 35, wherein said orthopedic rod includes an occipital rod.

37. The system of claim 35, further comprising an occipital plate coupled to said rod, said plate including:
   a cross-shaped member having a longitudinal axis connecting first and second longitudinal ends and a transverse axis connecting first and second transverse ends, said cross-shaped member having a plurality of apertures therethrough; and
   a plate saddle member coupled to said cross-shaped member, said plate saddle member having a plurality of upright portions that define a channel through said plate saddle member, wherein said rod is coupled in said channel.

38. The system of claim 37, further comprising a cross-link connector having a pair of coupling ends each adapted to couple to a rod and a cylindrical member provided between said coupling ends, one of said coupling ends being coupled to said rod.

39. The system of claim 21, further comprising:
   said orthopedic rod coupled to said offset member; and
   a bone attachment assembly coupled to said orthopedic rod and spaced apart from said saddle member, said bone attachment assembly for anchoring said rod to bone.

40. The system of claim 21, further comprising:
   said orthopedic rod coupled to said offset member;
   a second offset member spaced apart from said offset member, said second offset member having a second body coupled to said orthopedic rod and a second coupling member extending from said second body; and
   a bone attachment assembly spaced apart from said saddle member, said bone attachment assembly coupled to said second coupling member, said bone attachment assembly for anchoring said second offset member to bone.

41. The system of claim 21, further comprising:
   said orthopedic rod coupled to said offset member; and
   a cross-link connector having a pair of coupling ends each adapted to couple to a rod and a connecting member provided between said coupling ends, one of said coupling ends being coupled to said orthopedic rod.

42. The system of claim 21, further comprising:
   said orthopedic rod coupled to said offset member;
   a second offset member spaced apart from said offset member, said second offset member having a second body coupled to said orthopedic rod and a second coupling member extending from said second body;
   a bone attachment assembly spaced apart from said saddle member, said bone attachment assembly coupled to said second coupling member, said bone attachment assembly for anchoring said second offset member to bone; and
   a cross-link connector having a pair of coupling ends each adapted to couple to a rod and a connecting member provided between said coupling ends, one of said coupling ends being coupled to said orthopedic rod.

43. The system of claim 21, further comprising:
said orthopedic rod coupled to said offset member;
a second offset member spaced apart from said offset member, said second offset member having a second body coupled to said orthopedic rod and a second coupling member extending from said second body;
a bone attachment assembly spaced apart from said saddle member, said bone attachment assembly coupled to said second coupling member, said bone attachment assembly for anchoring said second offset member to bone;
a cross-link connector having a pair of coupling ends each adapted to couple to a rod and a connecting member provided between said coupling ends, one of said coupling ends being coupled to said orthopedic rod; and
an occipital plate coupled to said orthopedic rod, said plate including:
a cross-shaped member having a longitudinal axis connecting first and second longitudinal ends and a transverse axis connecting first and second transverse ends, said cross-shaped member having a plurality of apertures therethrough; and
a plate saddle member coupled to said cross-shaped member, said plate saddle member having a plurality of upright portions that define a channel through said plate saddle member, wherein said rod is coupled in said channel.

44. The system of claim 21, wherein said body of said offset member comprises a rod-receiving bore.

45. The system of claim 33, wherein at least one of said upright portions comprises a trough defined therein, and wherein said radially extending projection is positionable within said trough.

46. The system of claim 34, wherein said snap-ring comprises a non-planar body.

47. The system of claim 35, wherein said orthopedic rod comprises an upper plate portion and a lower rod portion.

48. An orthopedic fixation plate, comprising:
a cross-shaped member having a longitudinal axis connecting first and second longitudinal ends and a transverse axis connecting first and second transverse ends, said cross-shaped member having a plurality of apertures therethrough; and
a saddle member coupled to said cross-shaped member, said saddle member having a plurality of upright portions that define a channel through said saddle member.

49. The plate of claim 48, wherein said plate includes a plurality of saddle members attached to said cross-shaped member, each of said saddle members having a plurality of upright portions that define respective channels through said saddle members.

50. The plate of claim 48, wherein said saddle member is integral with said cross-member.

51. The plate of claim 48, wherein said saddle member is pivotally coupled to said cross-member.

52. The plate of claim 48, wherein said saddle member is located at one of said first and second longitudinal ends.

53. The plate of claim 48, wherein said channel of said saddle member has an axis, and said channel axis is substantially perpendicular to said longitudinal axis of said cross-shaped member.

54. The plate of claim 48, wherein said cross-member has at least one of said apertures at each of said first and second transverse ends of said cross-member.

55. The plate of claim 48, wherein said apertures are bounded by a surface having a conical portion.

56. The plate of claim 55, wherein said surface has an upper conical portion and a lower conical portion.

57. The plate of claim 48, wherein said cross-shaped member is curved.

58. The plate of claim 48, wherein said cross-shaped member is curved so that said longitudinal axis has a curved portion and said transverse axis is substantially straight.

59. The plate of claim 48, further comprising a first bone anchoring member positionable within one of said plurality of apertures to secure said plate to a bone.

60. The plate of claim 59, further comprising an orthopedic rod securable within said channel.

61. The plate of claim 60, further comprising a securing member cooperating with at least one of said plurality of upright portions to secure said orthopedic rod within said channel.

62. The plate of claim 60, further comprising a second bone anchoring member coupled to said orthopedic rod, said second bone anchoring member spaced apart from said first bone anchoring member.

63. The plate of claim 60, further comprising a cross-link connector having a pair of coupling ends each adapted to couple to a rod and a connecting member provided between said coupling ends, one of said coupling ends being coupled to said orthopedic rod.

64. A multi-axial bone attachment assembly, comprising:
a saddle member having a plurality of upright portions that define a channel through said saddle member, said saddle member further having a hole therethrough bounded by an inner wall, said hole forming a lower opening in said saddle member;
a bone anchoring member extending through said opening, said bone anchoring member including a coupling portion provided in said hole for permitting multi-axial movement of said anchoring member and an anchoring portion; and
an expansion member coupled to said anchoring member for expanding said coupling portion to lock said anchoring member into position.

65. The assembly of claim 64, wherein said anchoring portion includes a hook member.

66. The assembly of claim 64, wherein said coupling portion has a substantially spherical shape.

67. The assembly of claim 64, wherein said coupling portion includes a plurality of part spherical members.

68. The assembly of claim 64, wherein said expansion member is coupled to said anchoring member between said part spherical members.

69. The assembly of claim 64, wherein said expansion member includes a set screw.

70. The assembly of claim 64, wherein said expansion member includes a tool engaging portion, a threaded portion engaged with said coupling member, and a conically shaped expansion portion provided between said tool engaging portion and said threaded portion.

71. The assembly of claim 64, wherein said upright portions include threaded portions, and said assembly further comprises a threaded member for engagement with said threaded portions.

72. The assembly of claim 71, wherein said threaded portions have reverse angle threads.

73. The assembly of claim 64, further comprising an orthopedic rod securable within said channel.

74. The assembly of claim 73, further comprising a securing member cooperating with at least one of said plurality of upright portions to secure said orthopedic rod within said channel.

75. A multi-axial bone attachment assembly, comprising:
a saddle member having a plurality of upright portions that define a channel through said saddle member, said saddle member further having a hole therethrough bounded by an inner wall, said hole forming a lower opening in said saddle member;
a bone anchoring member extending through said opening, said bone anchoring member including a head portion and an anchoring portion;
a washer having a recessed portion for accommodating an orthopedic rod and a radially extending projection, said washer being fitted within said hole of said saddle member and atop said bone anchoring member; and
wherein said inner wall includes a groove, and said assembly further comprises a snap-ring fitted in said groove and over said washer to hold said washer in said hole of said saddle member.

76. The assembly of claim 75, wherein said upright portions include threaded portions, and said assembly further comprises a threaded member for engagement with said threaded portions.

77. The assembly of claim 76, wherein said upright portions are internally threaded, and said threaded member is an externally threaded set screw.

78. The assembly of claim 77, wherein said set screw includes an upper surface that is convexly rounded.

79. The assembly of claim 76, wherein said threaded portions have reverse angle threads.

80. The assembly of claim 75, wherein at least one of said upright portions has a trough defined therein, said radially extending projection of said washer disposed within said trough.

81. The assembly of claim 80, wherein said washer further comprises a lower surface, wherein said lower surface comprises a concave shape to coincide with a shape of said head portion of said bone anchoring member.

82. The assembly of claim 81, further comprising said orthopedic rod secured within said channel.

83. The assembly of claim 82, further comprising a cross-link connector having a pair of coupling ends each adapted to couple to a rod and a connecting member provided between said coupling ends, one of said coupling ends being coupled to said orthopedic rod.

84. The assembly of claim 81, wherein said saddle member further comprises a transverse hole defined through said upright portions that is transverse with respect to said channel, and further comprising an offset member adapted to couple to a rod, said offset member having a body adapted to couple to a rod and a coupling member extending from said body through said transverse hole in said upright portions.

85. The assembly of claim 84, further comprising said orthopedic rod secured within said body of said offset member.

86. The assembly of claim 85, further comprising a cross-link connector having a pair of coupling ends each adapted to couple to a rod and a connecting member provided between said coupling ends, one of said coupling ends being coupled to said orthopedic rod.

87. The assembly of claim 75, wherein said snap-ring comprises a non-planar body.

88. A multi-axial bone attachment assembly, comprising:
a saddle member having a plurality of upright portions that define a channel through said saddle member, said saddle member further having a hole therethrough bounded by an inner wall, said hole forming a lower opening in said saddle member;
a bone anchoring member extending through said opening, said bone anchoring member including a head portion and an anchoring portion;
a washer having a recessed portion for accommodating an orthopedic rod and a radially extending projection, said washer being fitted within said hole of said saddle member and atop said bone anchoring member;
wherein said washer includes an upper portion and a lower portion, said recessed portion being a part of said upper portion and said projection being a part of said lower portion; and
wherein said inner wall includes a groove, and said assembly further comprises a snap-ring fitted in said groove and over said lower portion of said washer to hold said washer in said hole of said saddle member.

89. The assembly of claim 88, wherein at least one of said upright portions has a trough defined therein, said radially extending projection of said washer disposed within said trough.

90. The assembly of claim 89, wherein said washer further comprises a lower surface, wherein said lower surface comprises a concave shape to coincide with a shape of said head portion of said bone anchoring member.

91. The assembly of claim 90, further comprising said orthopedic rod secured within said channel.

92. The assembly of claim 91, further comprising a cross-link connector having a pair of coupling ends each adapted to couple to a rod and a connecting member provided between said coupling ends, one of said coupling ends being coupled to said orthopedic rod.

93. The assembly of claim 90, wherein said saddle member further comprises a transverse hole defined through said upright portions that is transverse with respect to said channel, and further comprising an offset member adapted to couple to a rod, said offset member having a body adapted to couple to a rod and a coupling member extending from said body through said transverse hole in said upright portions.

94. The assembly of claim 93, further comprising said orthopedic rod secured within said body of said offset member.

95. The assembly of claim 94, further comprising a cross-link connector having a pair of coupling ends each adapted to couple to a rod and a connecting member provided between said coupling ends, one of said coupling ends being coupled to said orthopedic rod.

96. The assembly of claim 88, wherein said snap-ring comprises a non-planar body.

* * * * *

UNITED STATES PATENT AND TRADEMARK OFFICE
CERTIFICATE OF CORRECTION

PATENT NO.   : 6,485,491 B1
DATED        : November 26, 2002
INVENTOR(S)  : Farris et al.

It is certified that error appears in the above-identified patent and that said Letters Patent is hereby corrected as shown below:

<u>Drawings,</u>
Replace sheets 2-10, 12, 15-24, and 27-30 of 30, showing FIGS. 2-6, 6a, 7-17, 17a, 18, 24, 27-28, 28a, 29-45, and 48-56, with attached sheets showing FIGS. 2-6, 6a, 7-17, 17a, 18, 24, 27-28, 28a, 29-45, and 48-56.

Signed and Sealed this

Tenth Day of February, 2004

JON W. DUDAS
*Acting Director of the United States Patent and Trademark Office*

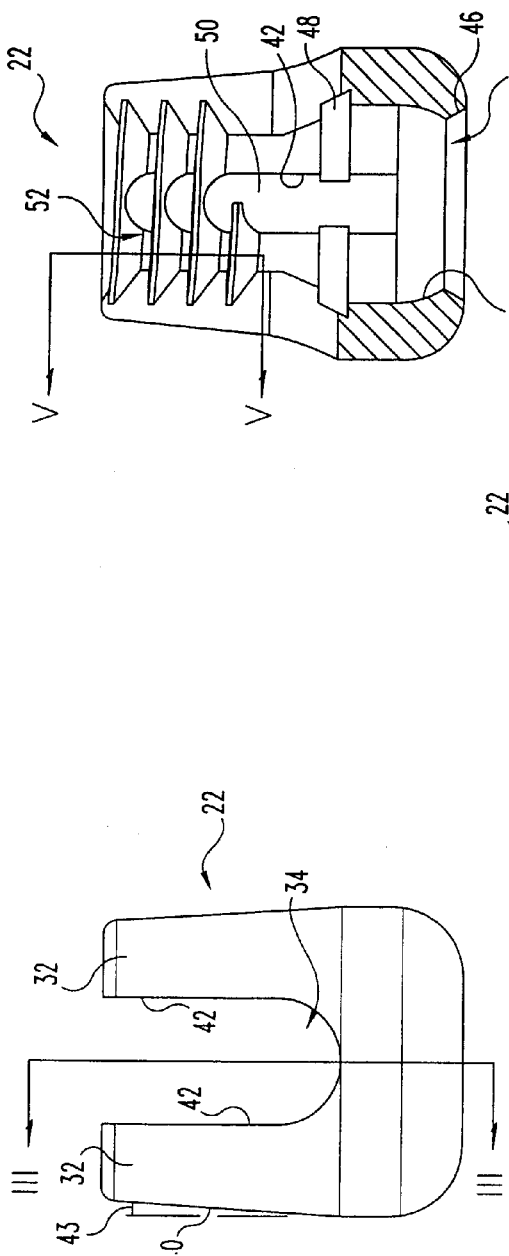
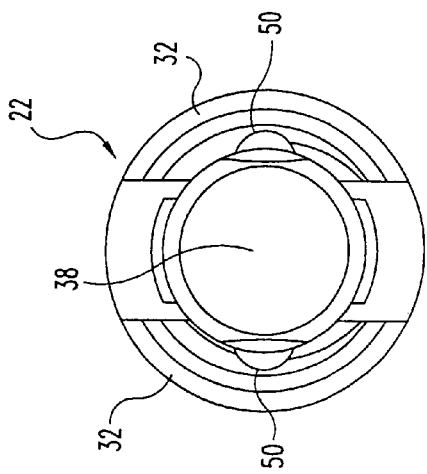
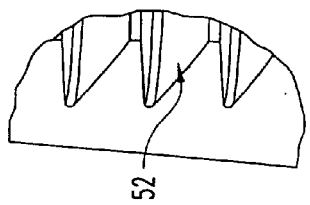
Fig. 2  Fig. 3  Fig. 4  Fig. 5

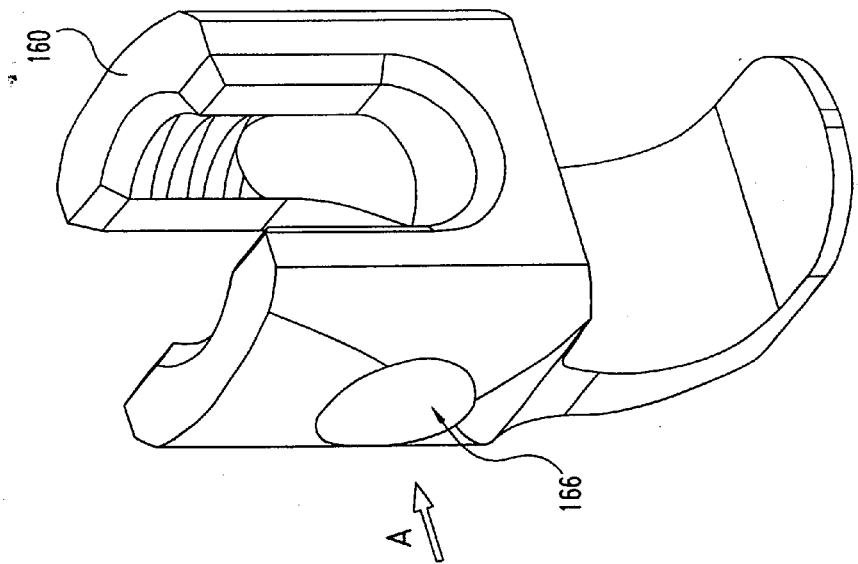
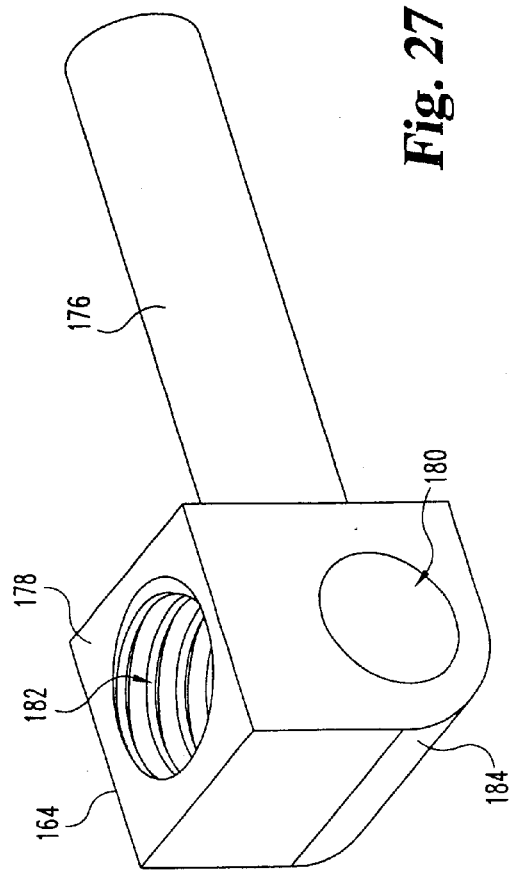
Fig. 27